(12) United States Patent
Griffiths et al.

(10) Patent No.: US 8,192,397 B2
(45) Date of Patent: Jun. 5, 2012

(54) MEDICAL FLUID INJECTION AND INFLATION SYSTEM

(75) Inventors: David M. Griffiths, Pittsburgh, PA (US); Rosemary Almon-Martin, Saxonburg, PA (US); Alan D. Hirschman, Glenshaw, PA (US); David M. Reilly, Glenshaw, PA (US); Frederick W. Trombley, III, Gibsonia, PA (US); Arthur E. Uber, III, Pittsburgh, PA (US); William Jaecklein, Ormond Beach, FL (US)

(73) Assignee: Medrad, Inc., Indianola, PA (US)

( * ) Notice: Subject to any disclaimer, the term of this patent is extended or adjusted under 35 U.S.C. 154(b) by 1238 days.

(21) Appl. No.: 11/425,497

(22) Filed: Jun. 21, 2006

(65) Prior Publication Data
US 2007/0197963 A1    Aug. 23, 2007

Related U.S. Application Data

(60) Provisional application No. 60/692,517, filed on Jun. 21, 2005.

(51) Int. Cl.
*A61M 29/00* (2006.01)
(52) U.S. Cl. .................................. 604/97.01
(58) Field of Classification Search ............ 606/192
See application file for complete search history.

(56) References Cited

U.S. PATENT DOCUMENTS

| | | | |
|---|---|---|---|
| 4,116,201 A | 9/1978 | Shah | |
| 4,147,170 A | 4/1979 | Taylor | |
| 4,280,501 A | 7/1981 | Foderick | |
| 4,332,254 A | 6/1982 | Lundquist | |
| 4,370,982 A | 2/1983 | Reilly | |
| 4,439,185 A | 3/1984 | Lundquist | |
| 4,559,036 A | 12/1985 | Wunsch | |
| 4,710,166 A | 12/1987 | Thompson et al. | |

(Continued)

FOREIGN PATENT DOCUMENTS

CA    2045070 A1    6/1991

(Continued)

OTHER PUBLICATIONS

International Preliminary Report on Patentability for Counterpart PCT Application No. PCT/US2006/024081, Form PCT/IB/373, WIPO, Dec. 24, 2007.

(Continued)

*Primary Examiner* — Nicholas Lucchesi
*Assistant Examiner* — Jason Flick
(74) *Attorney, Agent, or Firm* — David Schramm; Gregory L. Bradley

(57) ABSTRACT

A combined fluid injection and inflation system is disclosed and includes a fluid delivery system including at least one pressurizing device, a fluid path, and a control unit. The fluid path is adapted to connect the pressurizing device to a patient via a catheter including a balloon and inserted in the patient. The control unit is operable to control the fluid delivery system. In operation, the control unit selectively actuates the fluid delivery system to operate in a fluid injection mode or in a balloon inflation mode. In the fluid injection mode the pressurizing device delivers fluid to the fluid path for a fluid injection procedure. In the balloon inflation mode, the pressurizing device delivers fluid to the fluid path for inflating the balloon associated with the catheter. An operator control may be connected to the control unit for controlling the fluid delivery system and may be a handheld device.

14 Claims, 16 Drawing Sheets

U.S. PATENT DOCUMENTS

| | | | |
|---|---|---|---|
| 4,723,938 A | 2/1988 | Goodin et al. |
| 4,743,230 A | 5/1988 | Nordquest |
| 4,758,223 A | 7/1988 | Rydell |
| 4,808,165 A | 2/1989 | Carr |
| 4,832,692 A | 5/1989 | Box et al. |
| 4,919,121 A | 4/1990 | Rydell et al. |
| 4,925,444 A | 5/1990 | Orkin et al. |
| 4,940,459 A | 7/1990 | Noce |
| 5,015,233 A | 5/1991 | McGough et al. |
| 5,019,041 A | 5/1991 | Robinson et al. |
| 5,021,046 A | 6/1991 | Wallace |
| 5,135,488 A | 8/1992 | Foote et al. |
| 5,137,514 A | 8/1992 | Ryan |
| 5,147,300 A | 9/1992 | Robinson et al. |
| 5,152,776 A | 10/1992 | Pinchuk |
| 5,160,327 A | 11/1992 | Stines |
| 5,163,904 A | 11/1992 | Lampropoulos et al. |
| 5,199,604 A | 4/1993 | Palmer et al. |
| 5,201,753 A | 4/1993 | Lampropoulos et al. |
| 5,209,731 A | 5/1993 | Sterman et al. |
| 5,213,115 A | 5/1993 | Zytkovicz et al. |
| 5,215,523 A | 6/1993 | Williams et al. |
| 5,259,838 A | 11/1993 | Taylor et al. |
| 5,273,537 A | 12/1993 | Haskvitz et al. |
| 5,284,480 A | 2/1994 | Porter et al. |
| 5,290,260 A | 3/1994 | Stines |
| 5,300,027 A | 4/1994 | Foote et al. |
| 5,306,248 A | 4/1994 | Barrington |
| 5,318,533 A | 6/1994 | Adams et al. |
| 5,342,304 A | 8/1994 | Tacklind et al. |
| 5,385,549 A | 1/1995 | Lampropoulos et al. |
| 5,460,609 A | 10/1995 | O'Donnell |
| 5,599,301 A * | 2/1997 | Jacobs et al. ............... 604/65 |
| 5,840,026 A * | 11/1998 | Uber et al. ............... 600/431 |
| 6,416,493 B1 * | 7/2002 | Del Giglio ............... 604/96.01 |
| 6,731,971 B2 | 5/2004 | Evans, III et al. |
| 6,889,074 B2 | 5/2005 | Uber, III et al. |
| 7,241,273 B2 * | 7/2007 | Maguire et al. ............... 604/6.16 |
| 2004/0162488 A1 | 8/2004 | Uber, III et al. |
| 2005/0124971 A1 | 6/2005 | Koch et al. |

FOREIGN PATENT DOCUMENTS

WO     WO02/064195     8/2002

OTHER PUBLICATIONS

"Digital Injector for Angiography", SIAS, As early as Sep. 1993.

"The Solution for Our IV Formulas", IV 6500 Formulator Volumetric Pump, Valley Lab Inc., 39C 9410976 0000071 s, E-39-15, pp. 3399-3400, As early as 1980.

"Model 2681 Classic Syringe Infusion Pump with Two Syringe Capacity", BARD (C R) Inc./MedSystems 13E, 1249754 00000946 7, E-39-15, p. 2646, As early as 1974.

* cited by examiner

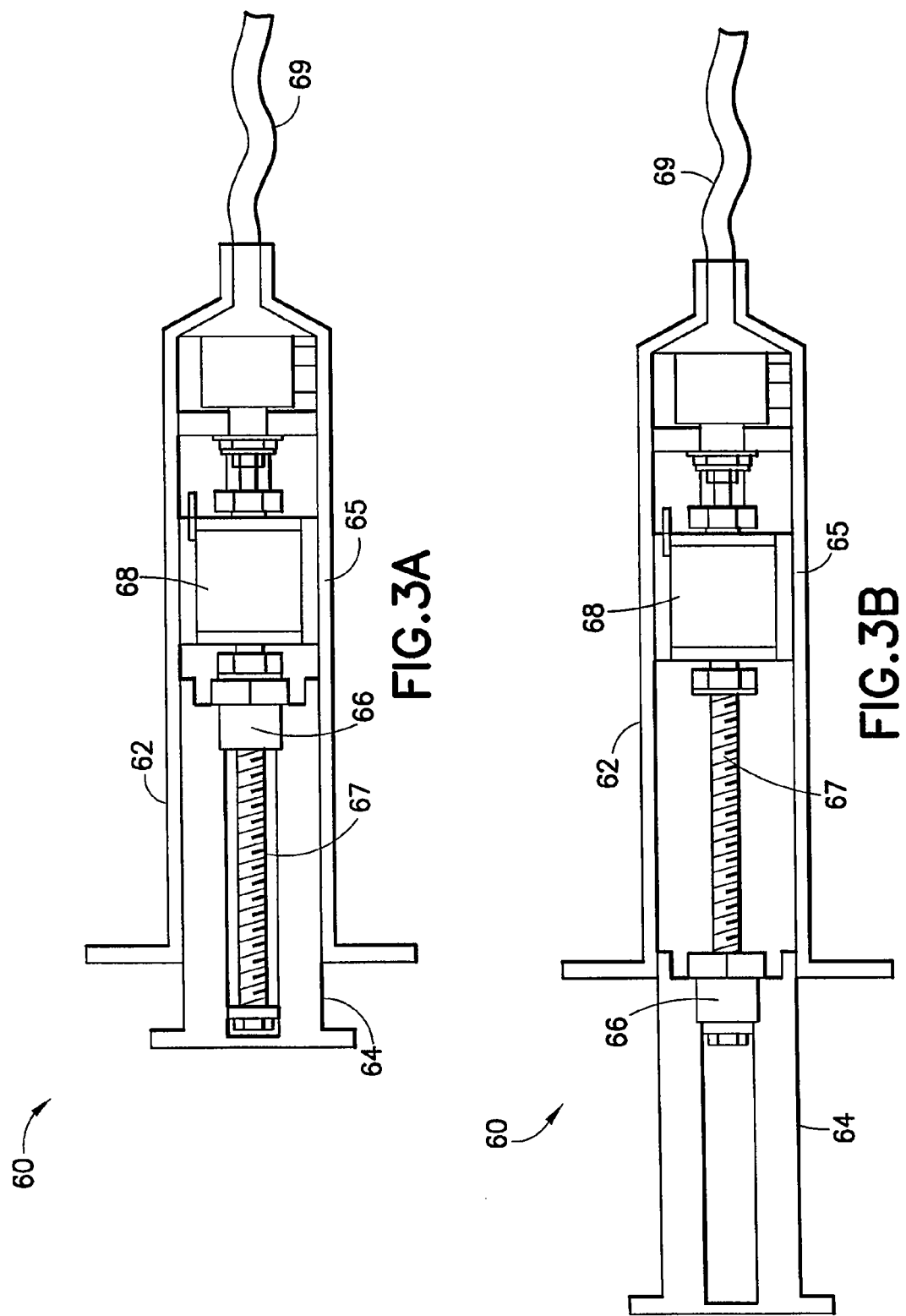

MEDICAL FLUID INJECTION AND INFLATION SYSTEM

CROSS REFERENCE TO RELATED APPLICATION

This application claims priority to and benefit of U.S. Provisional Patent Application No. 60/692,517 filed Jun. 21, 2005, the disclosure of which is incorporated herein by reference in its entirety.

BACKGROUND OF THE INVENTION

1. Field of the Invention

This invention relates to a combined fluid injection and inflation system that may be used to assist with both the diagnostic and therapeutic portions of percutaneous transluminal angioplasty (PTA), (balloon inflation/deflation), and with angioplasty procedures in general. The combined injection and inflation system is used to inject fluids such as contrast media ("contrast") for diagnostic imaging, catheter or guidewire placement, drug delivery or any similar fluid delivery application as well as to provide a balloon inflation capability for balloon angioplasty, balloon assisted stent deployment or other inflation applications. The system may be used with, but is not restricted to X-ray, MR, and ultrasonic imaging modalities, and generally comprises tactile, audible, and/or visual feedback capability so that a health care provider has more direct control of the fluid injection or inflation profile.

2. Description of Related Art

Several hundred thousand percutaneous transluminal coronary angioplasty (PTCA) procedures are performed in the United States each year in cardiac and special procedure imaging laboratories. In most instances, the angioplasty portion of the procedure is preceded by a diagnostic study that determines or confirms the degree and location of stenosis present. Angioplasty is a therapeutic approach that uses small inflatable balloons placed on the tip of a catheter to open blocked vascular tissue. A collapsed balloon is placed near the occluded area of the blood vessel and is inflated to apply pressure to the surface of the blockage and compress it against the blood vessel wall. Often, a power injector is in the procedure room for pre and/or post angioplasty studies to locate and determine the extent of stenosis or it is used for some other related diagnostic study, such as a ventriculogram, to determine heart function. In addition, it is sometimes used after a procedure to assess the effectiveness of any treatment.

Electromechanical devices for inflating balloons associated with catheters are known in the art and are now used as a supplement to or a replacement of manual inflation devices such as that described in U.S. Pat. No. 4,370,982 to Reilly. For example, U.S. Pat. No. 5,460,609 to O'Donnell discloses an automated inflation/deflation system for use in connection with a dilatation balloon catheter. The disclosed inflation/deflation system includes a fluid chamber having a plunger for pressurizing a body of inflation fluid in response to the movement of the plunger. Movement of the plunger is controlled by an electromechanical motor drive unit. The motor drive unit itself is activated in response to a signal directed from a control switch. The system further includes a pressure transducer and a display unit, so that the operator can monitor information relating to inflation pressure and inflation time. In addition, the system includes safety features for effectuating a rapid reduction in balloon pressure.

U.S. Pat. No. 5,273,537 to Haskvitz et al. discloses an inflation system which includes a frame-mounted pressure sensor to measure the pressure through a diaphragm on the exterior of a syringe, a microprocessor controlled display for inflation and duration information, and a control that allows motor-driven operation of inflation/deflation at selected rates or to selected specific inflation pressures. The syringe used in the system is disposable and driven by a plunger rod supported within the frame. The frame further supports a motor for driving the plunger. Other disclosed features of the system include a connected or wireless control means for controlling plunger advancement, piston release, and a display that indicates balloon volume, pressure, and inflation time information. This patent further discloses a control system that allows motor-driven operation of inflation/deflation at selected rates or to selected inflation pressures.

Published Canadian Patent Application No. 2,045,070 by Mizoguchi et al. discloses a syringe used in Digital Subtraction Angiography (DSA) and PTCA (percutaneous transluminal coronary angioplasty) that is driven by a motor. Motor velocity is controlled by a hand or foot control. The allowable ranges of control are preset in the control unit and displayed on a display unit together with control data.

U.S. Pat. No. 5,152,776 to Pinchuk discloses an automated balloon inflation device that uses an indirect pressure measurement as a source for feedback to implement pressure control by the inflation device. The overall system generally includes means for inflation/deflation patterning, a pump for withdrawing and dispensing fluid from a balloon, a pump drive mechanism, and a pressure control mechanism. One drawback with the system disclosed by this patent is the location of the control pressure transducer, which is specifically located between the pump drive mechanism and pump and is not likely to provide accurate pressure sensing information.

U.S. Pat. No. 5,021,046 to Wallace discloses a fluid pressure monitoring system for a balloon catheter that includes a pressure transducer in fluid communication with the interior of the balloon. The pressure transducer includes elements for providing an electrical signal which is a function of the pressure in the interior of the balloon. An electronic digital display is responsive to the electrical signal from the pressure transducer to display the balloon pressure measured by the pressure transducer. The system is adapted for use with a catheter that carries an inflatable balloon to the vicinity of a stenosis, where it is inflated, and the disclosed fluid pressure monitoring system detects and digitally displays to the operator the pressure inside the inflated balloon.

Furthermore, U.S. Pat. No. 5,385,549 to Lamproppoulos et al. discloses an electronically-controlled syringe system for connection to a balloon catheter or other balloon type member, and for automatically monitoring, displaying, and recording inflation data when the syringe system is used for inflation.

Devices for controlling administration of multiple intravenous solutions and medications are also known in the art. For example, U.S. Pat. No. 5,199,604 to Palmer et al. discloses an irrigation system for delivering a selected one of multiple liquid solutions to a treatment site. The irrigation system includes a plurality of solution reservoirs, each including a quantity of a respective liquid solution, a handpiece, a selector valve for fluidly coupling the handpiece to the selected solution and a pump for causing the selected solution to flow to the handpiece for delivery to the treatment site. The irrigation system also includes a heater for heating the liquid solution prior to its delivery to a patient.

U.S. Pat. No. 4,925,444 to Orkin et al. discloses a multiple fluid delivery system adapted to deliver intravenous fluids to a patient from a plurality of fluid sources. The system includes flexible tubing for coupling the respective sources to a fluid junction member. The fluid junction is coupled by an output conduit to a controllable pump which is connected to a patient catheter. The system is adapted to multiplex a plurality of different fluids. The fluids may be mixed in the output conduit as desired. Operator interaction and control of the system occurs either through a display screen or by means of a bar code sensor.

U.S. Pat. No. 4,559,036 to Wunsch discloses an apparatus for sequentially dispensing a plurality of solutions through an intravenous supply catheter to a patient. The system includes a disposable tubing manifold that is connected to each of the solutions to be administered. Valves mounted upon a manifold plate stop flow of solution through the branches of the tubing manifold which engages each branch. The quantity of solution dispensed is metered by a volumetric infusion pump and controlled by sequentially opening and closing the valves individually. Electronically operable motors or solenoids are connected to each valve for automatically opening and successively closing each valve. A sequencer-timer in accordance with a predetermined program controls the automatic energization and successive de-energization of each motor, one at a time, and successively energizes additional motors for intermittent individual operation through a pre-selected cycle of operation.

Furthermore, U.S. Pat. No. 4,710,166 to Thompson et al. discloses a system for sequentially administering to a patient fluids from a secondary fluid container and a primary fluid container at respective selected flow rates governed by an electromechanical device that includes a pump. The system includes a Y-connector upstream from the electromechanical device, a primary fluid line extending from the primary fluid container through a primary valve to the Y-connector, and a secondary fluid line extending from the secondary fluid container to the Y-connector through a secondary valve. An output flow line extends from the Y-connector to the pump associated with the electromechanical device.

Other relevant fluid delivery systems are disclosed in U.S. Pat. No. 6,889,074 and U.S. Patent Application Publication No. 2004-0162488 to Uber, III et al. ("Uber") and U.S. Pat. No. 6,731,971 to Evans, III et al. ("Evans"). Generally, these patents disclose medical devices for delivery of contrast to a patient while allowing the adjustment of contrast concentration and injection parameters either before or during an injection procedure to provide patient specific dosing of contrast. Uber discloses a fluid delivery system comprising first and second sources of fluid medium, first and second pressurizing devices associated with the first and second sources of fluid medium, a fluid path operable to deliver the first and second fluid media to a balloon catheter inserted in a patient, and a control unit in communication with the pressurizing devices. Evans discloses a fluid delivery system similar to that disclosed by Uber but the first and second pressurizing devices are selectively operable to deliver the first fluid medium or the second fluid medium to the fluid path. This system is further directed to enabling the injection of fluid media into a plurality of patients. Generally, the system disclosed by Evans includes a fluid supply source providing multiple doses of fluid media, a metering device for measuring the doses, a pressurizing device to effect injection, a contamination prevention device disposed between the fluid source and patient and, if desired, and electronic control device.

SUMMARY OF THE INVENTION

The invention described herein improves upon the foregoing balloon inflation systems by being able to serve as both a fluid injection system and a balloon inflation system. Additionally, the invention disclosed herein improves upon the foregoing multiple fluid delivery systems by being capable of delivering such multiple fluids, individually or in combination, under pre-selected injection pressures while retaining a high-pressure fluid injection capability and/or a balloon inflation-deflation capability.

In general, the invention is a system that provides multiple fluid delivery modes including a fluid injection mode and a balloon inflation mode, obviating the need for multiple and separate pieces of equipment to perform these functions. In addition, it allows for coordinated or automated synchronization of fluid injection, balloon inflation, and aspiration. Balloon inflation may be performed for a lower cost per patient since the system is reusable, with the exception of a few inexpensive per-patient disposable components. Unlike the prior art devices discussed previously, the human operator has active, continuous control of the system, for example, through the use of a hand controller that allows for single-handed operation. The operator may continuously operate the system based on real-time fluid parameter feedback data provided to the operator. The system provides a level of tactile feedback to the operator increasing the operator's sense of control. Also, the system allows a "sensitivity adjustment" that varies the degree of tactile feel. Additionally, higher fluid pressures and flow rates may be obtained in the present system than can be achieved by hand syringes. Further, a large reservoir may be used and the system may be configured for automatic loading and reloading so that the system fluid path may remain closed for multiple injections, so as to lessen or eliminate the possibility of introducing air into the fluid path which may be harmful to the patient. Moreover, the system is adapted to support programmed limits and indicators for flow, volume, and pressure when injecting or inflating fluid even while the operator uses an operator control such as a hand controller or foot controller.

The medical fluid injection and inflation system, in one embodiment, generally comprises a fluid delivery system comprising at least one pressurizing device, a fluid path adapted to connect the at least one pressurizing device to a patient via a catheter comprising a balloon and inserted in the patient, and a control unit. The control unit is operable to control the fluid delivery system, wherein the control unit selectively actuates the fluid delivery system to operate in a fluid injection mode wherein the at least one pressurizing device delivers fluid to the fluid path for a fluid injection procedure, or in a balloon inflation mode wherein the at least one pressurizing device delivers fluid to the fluid path for inflating the balloon associated with the catheter.

The control unit may comprise an operator interface to input fluid injection mode and balloon inflation mode parameters for the selected procedure. The operator interface may be commonly housed with the at least one pressurizing device.

The at least one pressurizing device may comprise a syringe pump and the control unit may control operation of the syringe pump via a pump controller. The fluid injection and inflation system may further comprise an operator control connected to the control unit, such as a handheld control device.

Additionally, an embodiment of the invention is directed to using the fluid injection and inflation system as a platform for delivering fluid to a catheter comprising a balloon and inserted in a patient. Such a method typically comprises providing a fluid delivery system comprising at least one pressurizing device, a fluid path adapted to connect the at least one pressurizing device to the catheter, a control unit operable to control the fluid delivery system, and an operator control connected to the control unit. Fluid injection and/or balloon inflation parameters is then inputted into the control unit for performing a fluid injection procedure and/or a balloon inflation procedure. Once the parameters are inputted, an operator may actuate the operator control to perform either the fluid injection procedure or balloon inflation procedure whereby fluid is delivered to the catheter in accordance with the fluid injection or balloon inflation parameters inputted into the control unit.

In another embodiment, the fluid injection and inflation system generally comprises a fluid delivery system comprising at least one pressurizing device connected to at least one fluid source, a fluid path adapted to connect the at least one pressurizing device to a patient via a catheter inserted in the patient, the catheter comprising a fluid injection lumen and a balloon inflation lumen for inflating a balloon associated with the catheter, and a control unit operable to control the fluid delivery system. The control unit selectively actuates the fluid delivery system to operate in a fluid injection mode wherein the at least one pressurizing device delivers fluid to the fluid injection lumen via the fluid path for a fluid injection procedure, or in a balloon inflation mode wherein the at least one pressurizing device delivers fluid to the balloon inflation lumen for a balloon inflation procedure wherein the balloon associated with the catheter is inflated with fluid.

The at least one fluid source may comprise a first fluid source containing contrast and a second fluid source containing a diluent media. The at least one pressurizing device may deliver contrast from the first fluid source to the fluid injection lumen in the fluid injection mode, and deliver a mixture of contrast and diluent from the first and second fluid sources to the balloon inflation lumen in the balloon inflation mode.

In one form, the at least one pressurizing device comprises a syringe pump. The at least one pressurizing device may comprise a first pressurizing device and a second pressurizing device each selectively connectable to at least two different fluid sources. Accordingly, the first pressurizing device delivers fluid from a first fluid source to the fluid injection lumen in the fluid injection mode, and the second pressurizing device delivers a mixture of fluids from the first fluid source and the second fluid source to the balloon inflation lumen in the balloon inflation mode. The first fluid source may comprise contrast and the second fluid source may comprise a diluent.

As indicated previously, the at least one pressurizing device may comprise a first pressurizing device and a second pressurizing device. The first pressurizing device may be selectively connectable to at least two different fluid sources and the second pressurizing device is desirably selectively connectable to a third fluid source. In one example, the first pressurizing device delivers fluid from the first fluid source to the fluid injection lumen in the fluid injection mode and delivers a mixture of fluids from the first fluid source and the second fluid source to the balloon inflation lumen in the balloon inflation mode. In another example, the second pressurizing device delivers fluid from the third fluid source to the fluid injection lumen in the fluid injection mode.

In a further embodiment, the invention is directed to a fluid injection and multi-fluid delivery system. This system generally comprises a multi-fluid delivery apparatus comprising a plurality of fluid sources containing fluid media, a plurality of fluid control valves respectively associated with the fluid sources, a fluid mixing device for mixing fluids from the fluid sources, and a fluid pump for delivering a fluid or a mixture of fluids from the fluid sources to a catheter inserted in a patient. The system includes at least one pressurizing device connected to a source of contrast and a fluid path adapted to connect the at least one pressurizing device to the catheter. The catheter typically comprises a first lumen and a second lumen, the fluid path connected to the first lumen and the fluid pump connected to the second lumen. A control unit is operable to control the control valves and the at least one pressure device. The control unit selectively actuates the at least one pressurizing device to deliver contrast to the first lumen via the fluid path and the fluid pump to deliver a fluid or a mixture of fluids from the fluid sources to the second lumen. A balloon is typically associated with the second lumen and the fluid pump is adapted to inflate the balloon with a mixture of fluids from the fluid sources.

Further details and advantages of the invention will become clear upon reading the following detailed description in conjunction with the accompanying drawing figures, wherein like parts are identified with like reference numerals throughout.

BRIEF DESCRIPTION OF THE DRAWINGS

FIGS. 3A and 3B are cross-sectional views, without cross hatching, of an electromechanical control device for controlling fluid delivery from the fluid injection and inflation system identified in block form in FIG. 1.

DESCRIPTION OF THE PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Figure 1:
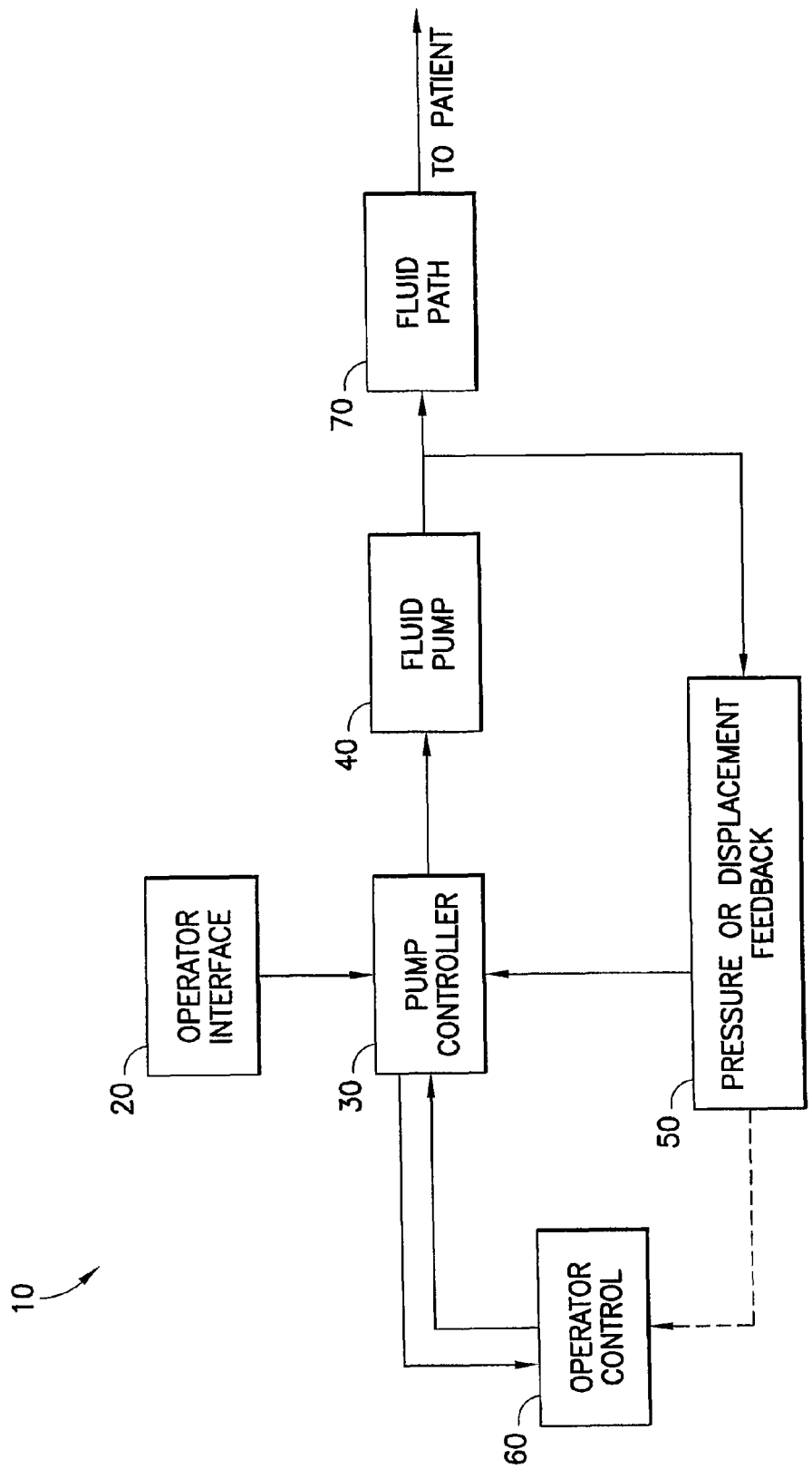
FIG. 1 is a block diagram showing the major components of a combined fluid injection and inflation system.
Figure 4:
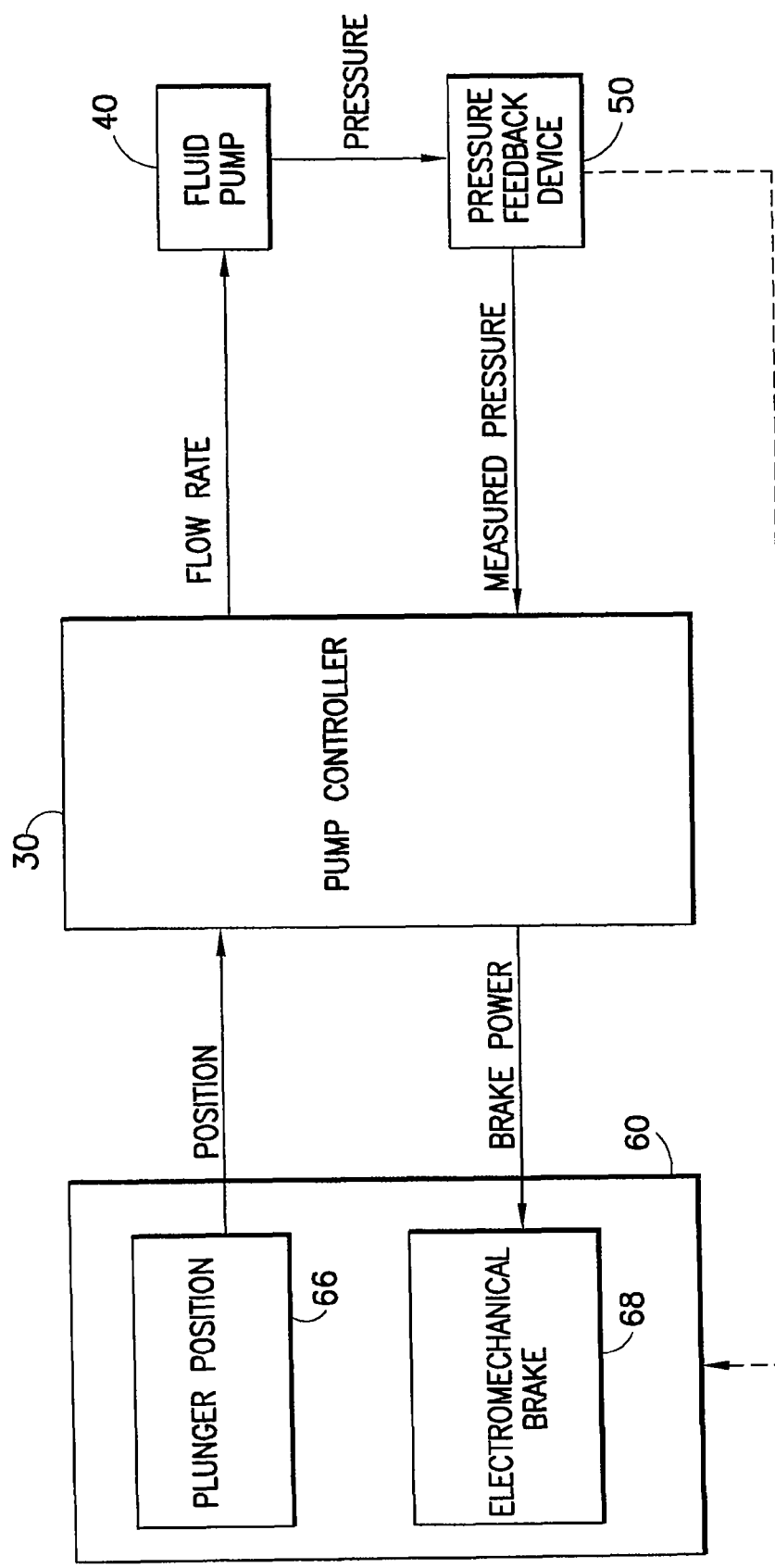
FIG. 4 is a block diagram representative of control circuitry for controlling the electromechanical device of FIGS. 3A and 3B.
Figure 5:
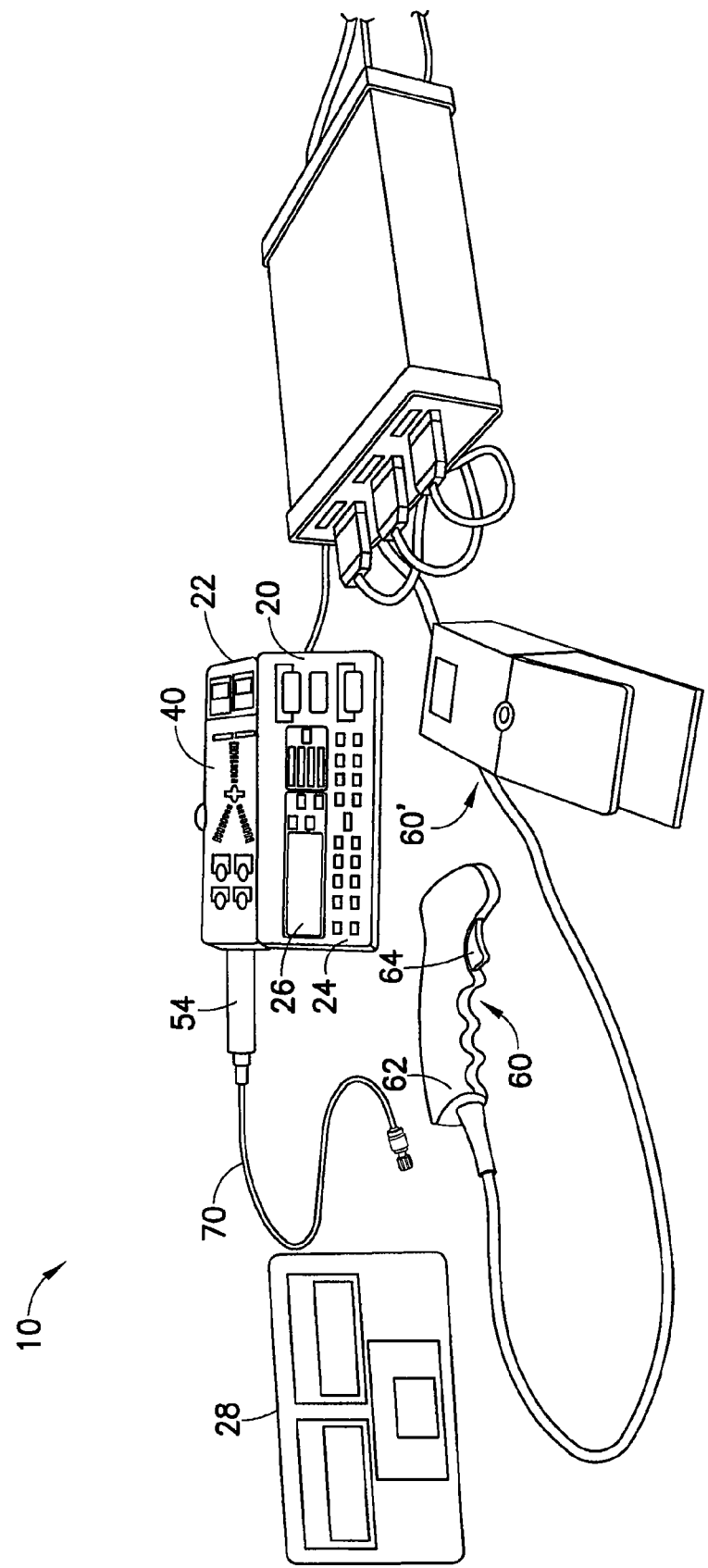
FIG. 5 is a perspective view of the fluid injection and inflation system showing its individual components.
Figure 6:
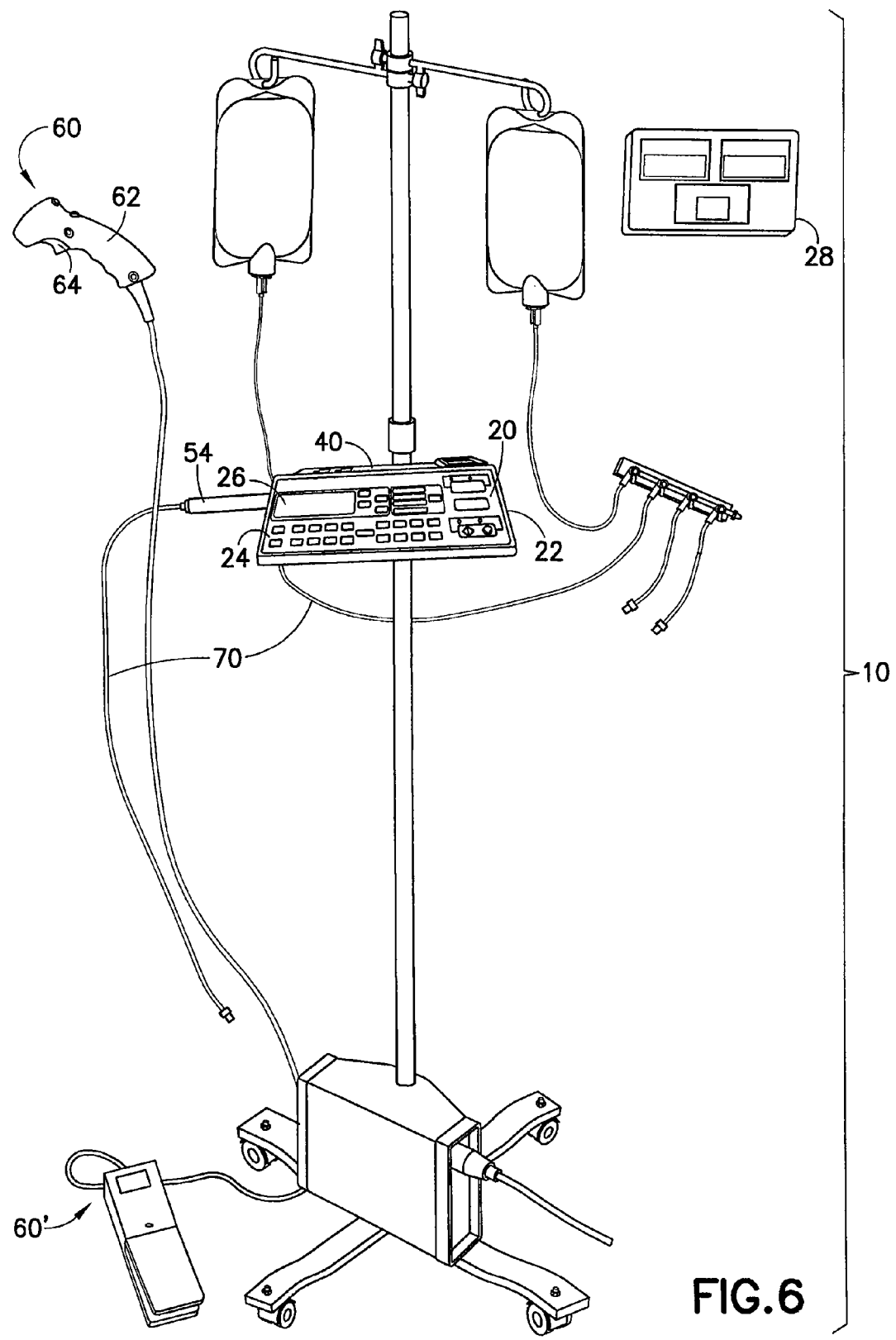
FIG. 6 is a perspective of the fluid injection and inflation system of FIG. 5 shown supported on a mobile base.
Figure 7:
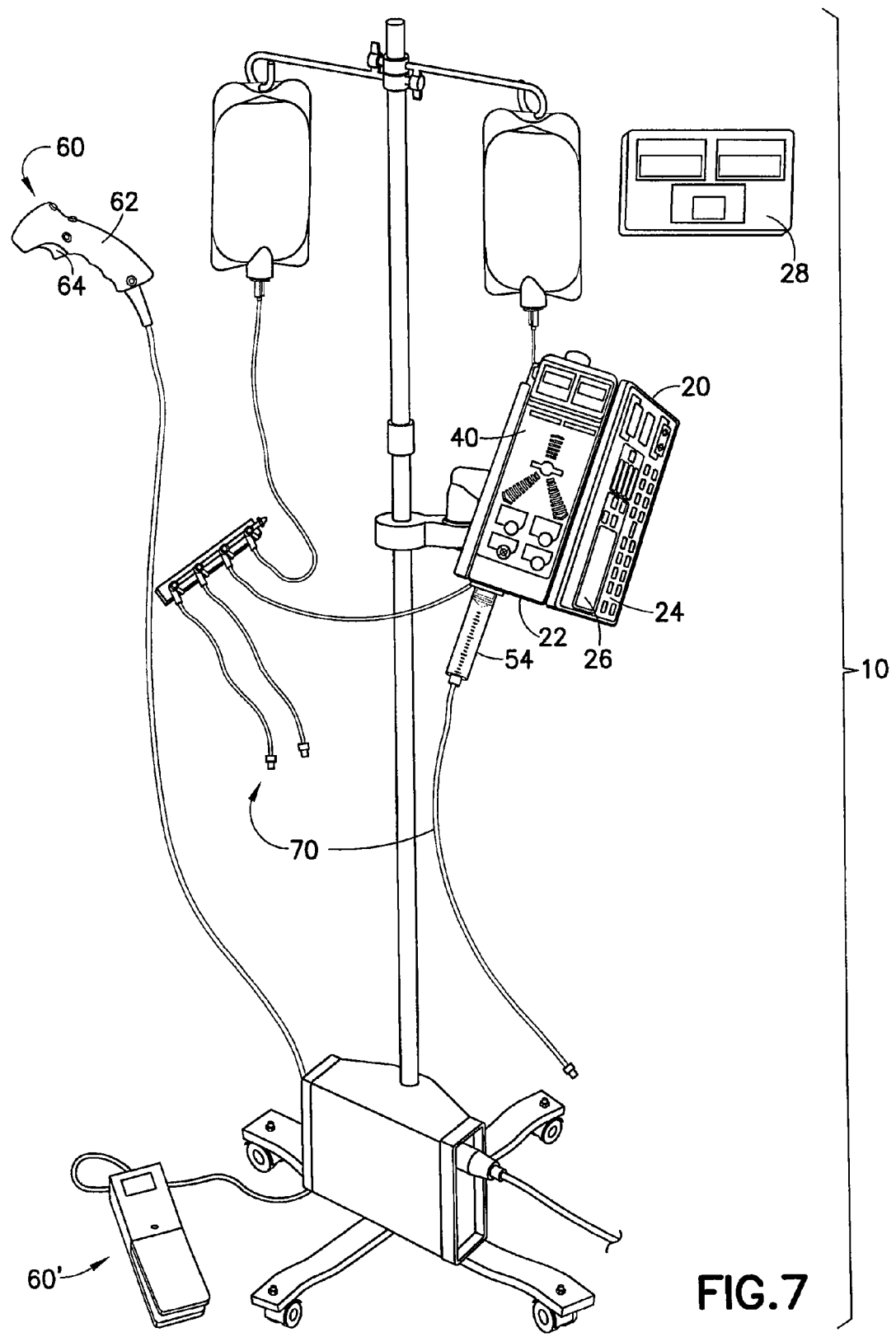
FIG. 7 is a perspective of the fluid injection and inflation system of FIG. 6, showing a fluid injector of the system pivoted to a different position.
Figure 8:
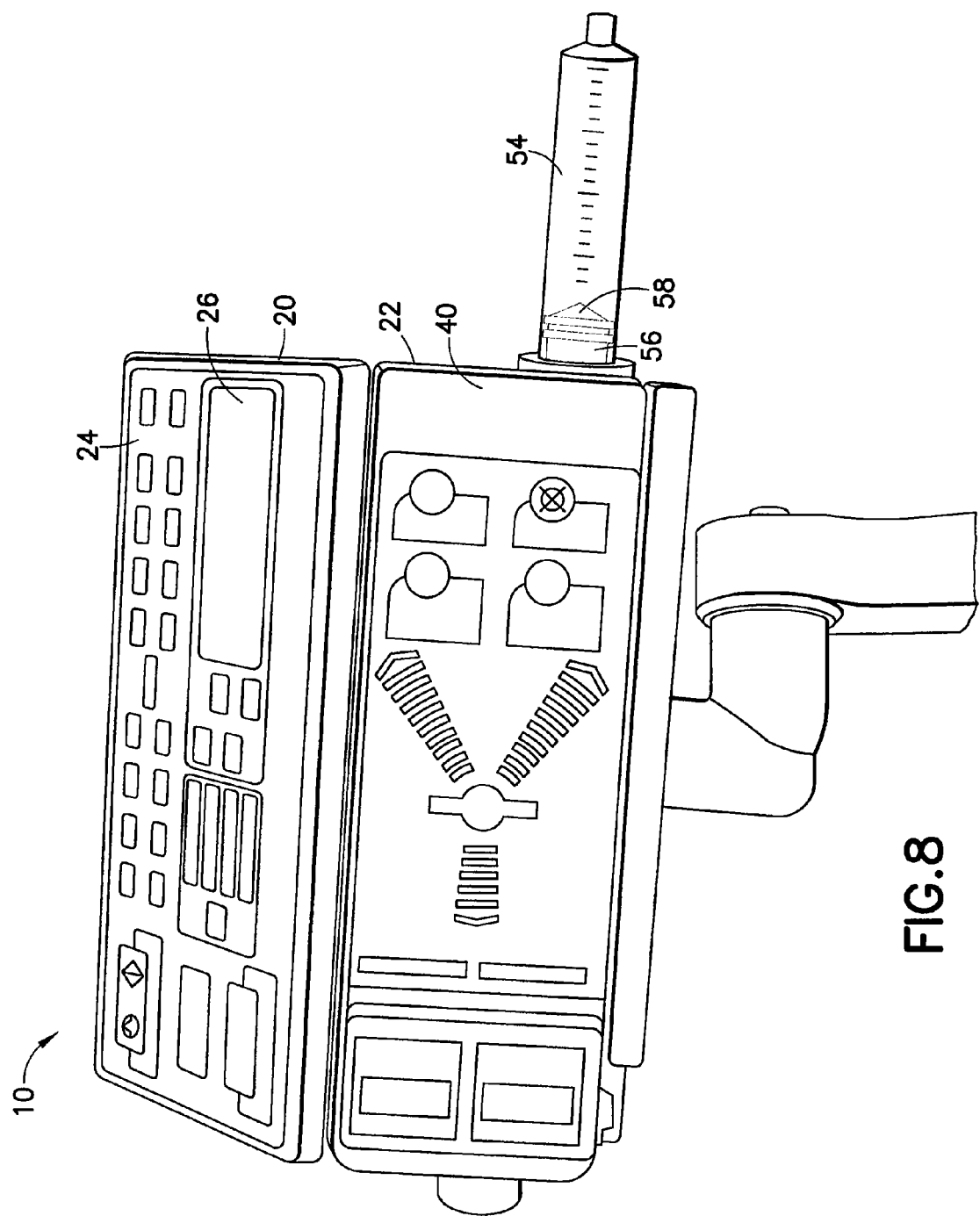
FIG. 8 is a top perspective and isolation view of an operator interface and fluid injector of the fluid injection and inflation system of FIG. 5.
Figure 9:
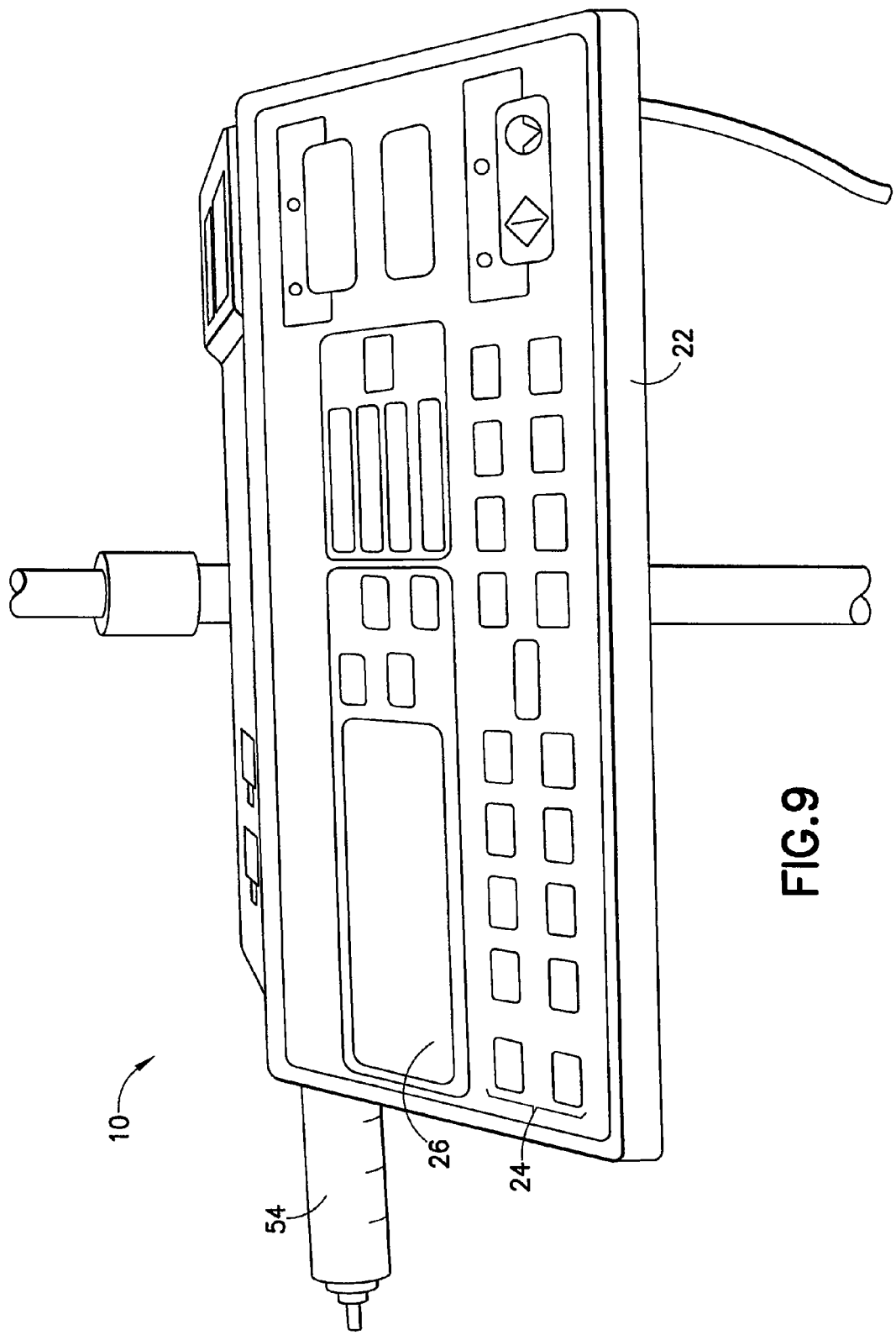
FIG. 9 is a side perspective and isolation view of the operator interface and fluid injector of the fluid injection and inflation system of FIG. 5.
Figure 10:
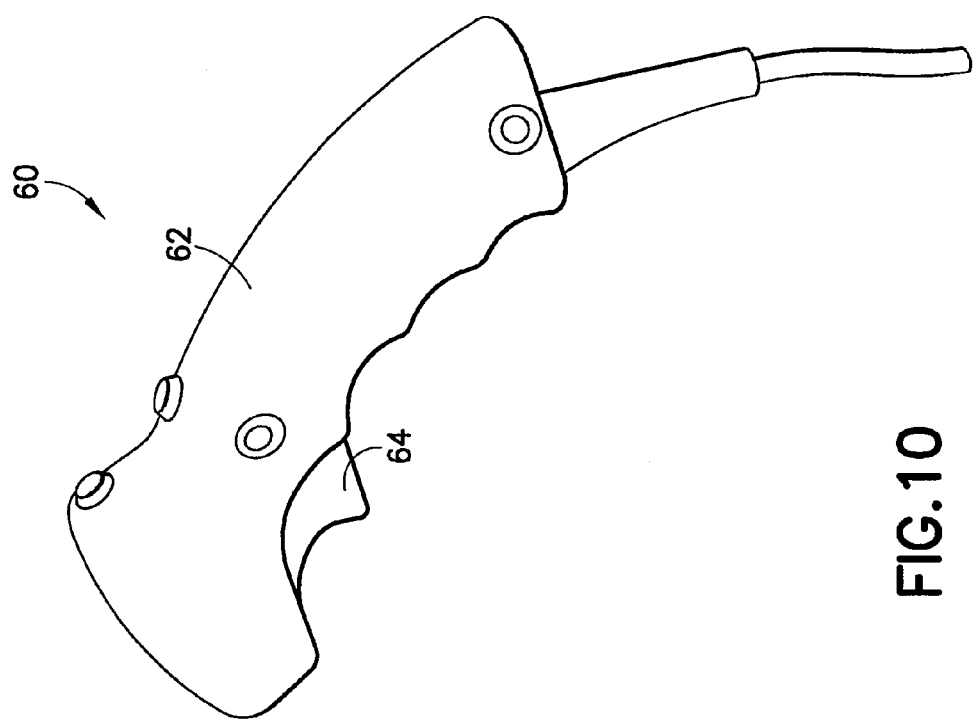
FIG. 10 is a side view of a hand controller embodiment of the electromechanical control device of FIG. 3A and 3B.

FIG. 1 is a block diagram showing the basic components of a fluid injection and inflation system 10 (hereinafter "system 10") pursuant to an embodiment of the invention. Generally, system 10 includes a plurality of operatively connected components, comprising: (1) an operator interface 20; (2) a pump controller 30; (3) a fluid pump 40; (4) a fluid parameter feedback device 50; (5) an operator control 60; and (6) a fluid path 70. Operator interface 20 is generally adapted to accept operator inputs regarding fluid injection and/or inflation parameters before the fluid injection or fluid inflation action occurs, displays status information, allows basic control functions to be selected, and communicates information to pump controller 30. Pump controller 30 is generally adapted to accept fluid injection/inflation parameters from operator interface 20, receive direction from operator control 60, and control the actions of fluid pump 40. Operation of fluid pump 40 is generally directed by pump controller 30, and is used to generate fluid pressure and volume displacement or fluid flow required for the fluid injection and/or inflation procedure. Feedback device 50 may comprise multiple forms but is typically comprised of sensors placed near fluid pump 40 for detecting pressure or, for example, piston position from which fluid displacement (e.g., volume), fluid flow rate, and fluid acceleration may be derived. Pressure may be measured via a pressure transducer at the fluid output of system 10 or an estimate of fluid pressure may be obtained based on power requirements and flow (e.g., power=flow×pressure) of fluid pump 40. System feedback to the operator may also include displacement data related to fluid pump 40. Displacement may be measured at pump controller 30 or with a position sensor at fluid pump 40, or by a sensor placed in fluid path 70. As shown in FIGS. 1 and 4, operator control 60 optionally receives pressure or displacement feedback signals from feedback device 50, communicates such signals in audible, visual, or tactile form to the operator, receives force or displacement or other control commands from the operator, and communicates these commands to pump controller 30, all in a continuous or periodic manner. Pump controller 30 controls operation of fluid pump based, in part, on the information received from operator control 60. Alternatively and presently preferred, pump controller 30 receives pressure or displacement feedback signals directly from feedback device 50. Pump controller 30 then communicates such signals in audible, visual, or tactile form to the operator via operator control 60, all in a continuous or periodic manner. Finally, output of fluid pump 40 is connected to fluid path 70 which is connected to a catheter (shown in FIGS. 15-18) that is intravenously inserted into a patient. In the case of a diagnostic study, the catheter fluid injection lumen is typically open at the tip so that radiopaque contrast media (hereinafter "contrast") may be delivered to the patient. In the case of an angioplasty procedure, the catheter contains a lumen for an inflatable balloon at the tip of the catheter for opening blood vessels. The fluid injection lumen may also be used for delivering a selected drug to the patient at an intended location.

With each of the components of system 10 generally identified, additional features of each component will now be discussed with reference to FIGS. 1-10. Operator interface 20 performs several functions including, but not limited to: (1) receiving operator input for fluid injection and inflation parameters; (2) determining system configuration or operating modes; (3) accepting operator programming as well as to display relevant information. Operator interface 20 is typically housed within a common housing 22 with fluid pump 40. Operator interface 20 comprises a parameter input device, such as a keyboard 24, or pre-identified identified command buttons. Other possible parameter input devices include, but are not limited to, a touch screen and display, rotary controls, levers, or other actuators. Voice operation may also be provided as long as an alternative input is available in the case of voice recognition failure or operator laryngitis. Additionally, operator interface 20 may comprise a display screen 26 for viewing the input commands and confirming the commands before they are committed to machine memory.

Operator interface 20 is used to input parameters that may be constant during, for example, a fluid injection procedure or inflation procedure. Operator control 60, however, is provided to allow the operator to modify the delivery of fluid when operating system 10 in a fluid injection mode or an inflation mode, or provides an activate/deactivate (on-off) function for the operator. More specifically, when fluid pump 40 is to perform a fluid injection operation (e.g., operate as a fluid injector), examples of typical programmed parameters for the fluid injection operation may include: volume, flow rate profile, pressure limit, flow rate acceleration or deceleration, injection duration, time delays (e.g., pause or hold functioning), and external triggering or interface options. Alternatively, when fluid pump 40 is to perform a fluid inflation procedure (e.g., operate as an inflator), examples of typical programmed parameters for the fluid inflation operation may include: volume limit, inflation rate limit, pressure limit, timing trigger pressure thresholds, pressure or duration alarm settings, and external interface or triggering options. Settings for fluid injection and inflation may be preprogrammed into machine memory and recalled before the beginning of each procedure. An external display 28 remote from operator interface 20 may also be provided that continuously displays real-time operational data during the fluid injection or inflation procedure. External or remote display 28 may be hard-wired to operator interface 20 or be connected wirelessly to operator interface 20.

One operational feature of operator interface 20 is an adjustable pressure threshold trigger that is used to start and/or terminate inflation timing on inflation time displays. Accordingly, only the inflation duration above some minimum pressure is timed, providing more accurate information on the time that a lesion or constriction is actually under stress from an angioplasty balloon as an example. Operator interface 20 may also be used to program thresholds to alarm or alert to the operator when preprogrammed pressure or duration milestones have been reached or exceeded. The alarm or alert mechanism could be audible with tones of different pitch indicating pressure or duration achieved, or visual with indicators showing the pressure or duration achieved during the fluid injection or inflation. Such a visual alarm could entail remote display 28 entering an intermittent blinking mode or another visual cue to alert the operator. Moreover, the alarm or alert could even be tactile, generating a response in operator control 60, which may be a handheld device as described herein. Such a response could be through vibration of the hand controller, additional resistance to motion, or even a measured backward displacement of a plunger within a syringe associated with fluid pump 40.

Operator interface 20 is also used to display current fluid injection or inflation status and history thereof with respect to pressure, timing, and number of fluid injections or inflations. Such information may be display on display screen 26 or remote display 28 or be divided between these two displays. For example, remote display 28 may be large in size and be wall-mounted to show fluid injection/inflation pressure, duration, and number of fluid injections/inflations. Remote display 28 may desirably be placed near the fluoroscopic monitors or other monitors in a procedure room so that they are highly visible to operating personnel. Multiple remote displays 28 may also be provided, with each remote display 28 wired or wireless connected to operator interface 20. Suitable wireless transmission methods include, but are not limited to, using radio frequency, infrared, ultrasonic, or carrier current signal transmission techniques, and suitable equivalent. It is also possible to combine multiple display outputs with the signals for video monitors in the procedure room, so that fluid injection/inflation parameters may be presented to the operator near the fluoroscopic or DSA (Digital Subtraction Angiography) image. For example, data intended for display screen 26 or remote display 28 may be overlaid onto the video monitors in the procedure room to reduce the number of displays the operator must consult to obtain an accurate picture of the status of the fluid injection/inflation procedure.

A further feature of operator interface 20 is the ability to keep track of the elapsed time between fluid injections/inflations. This information is useful for multiple inflations performed on a lesion. In general, information on inflation timing and the count of the number of inflations is most useful on a per lesion basis (e.g., procedure information is typically recorded as number of inflations, inflation time, and pressure maintained for each lesion). A feature that allows an operator to indicate application to a new lesion may also be provided.

As with many types of available medical equipment, system 10 may include a printer to provide a hard copy of fluid injection/inflation status and programmed settings. Information on fluid injection/inflation status and settings may also be linked to information systems for the laboratory or with other systems for documentation and record keeping. Operator interface 20 may be entirely physically separate from fluid pump 40 and the other components of system 10, or physically integrated and distributed among the various components of system 10. Moreover, some basic controls that set volume, pressure, or other similar parameters may reside on the hand controller for operator convenience.

As indicated previously, pump controller 30 receives desired fluid inflation and injection inputs and commands from operator interface 20 and receives continuous or periodic (e.g., discrete) input/commands from operator control 60. In one form, the input may be continuously varying commands from operator control 60. Pump controller 30 causes fluid pump 40 to execute a fluid injection or inflation profile based on input from operator interface 20 and/or operator control 60. For example, pump controller 30 may provide automatic fluid inflation and deflation based on programmed settings, semi-automatic operation with the programmed settings providing limits on the inflation parameters (e.g., inflation time, or maximum achieved pressure), or allow the inflation profile to be controlled strictly by operator control 60. For example, fully automated fluid inflation would inflate a balloon to a preset pressure for a preset time period at a preset pressure, and then automatically deflate. Multiple or profiled fluid inflations could also be automatically performed. A semi-automated fluid inflation mode provides automatic deflation after pressure has been maintained with operator control 60 for a preset time period. A manual inflation mode would be controlled entirely by operator control 60, with the operator determining the inflation pressure and duration as the fluid inflation occurs. In another example, it may be useful to allow for rapid deflation and aspiration or withdrawal of fluid when a sudden pressure decrease is detected in order to remove debris or particulate matter that is dislodged during the angioplasty procedure as described further herein.

In another example, a preprogrammed setting to limit the inflation rate or pressure increase may be useful in reducing the incidence of arterial dissection due to a large rate of increase in balloon force against the blood vessel wall. Another useful feature of pump controller 30 is the ability to oscillate the balloon inflation pressure about some set-point that is between two limits to ease balloon positioning and placement in the blood vessel near a point or region of interest. A feature to maintain pressure or volume at a value or between two limits would be applicable to fluid inflation and injection uses. Another useful feature of pump controller 30 is the ability to stop a fluid inflation if a sudden decrease in inflation pressure occurs while inflating. A sudden pressure decrease could be an indication of balloon failure. Terminating the inflation, or even drawing back a small volume reduces the potential for additional fluid and possibly, air from being delivered to the patient.

Pump controller 30 further includes a memory feature that automatically records and repeats a profile of a prior inflation based on information inputted from operator control 60. This profile could then be used on subsequent inflations at that lesion or other lesions. One of such stored profiles may be a profile for balloon integrity test. This profile could be accessed to perform a test inflation of a balloon to check balloon integrity and check for leaks. A further stored profile could be provided to automatically and repeatedly fill and empty the balloon to purge the air from an inflation balloon before use. Finally, during balloon deflation, pump controller 30 may be adapted ensure that fluid pump 40 generates controlled precise negative pressure so that the contrast/saline mixture in the balloon is quickly drawn out and the balloon profile (e.g., volume) is minimized to ease extraction from the patient's body. This action could also be provided as a stored profile in pump controller 30. It will be understood that the memory feature of pump controller 30 could be integrated into operator interface 20 or other components of system 10. Separate displays may be provided on display screen 26 or remote display 28 for the foregoing stored profiles/functions associated with pump controller 30. For example, due to the need to cause quick deflation of a balloon should a medical emergency arise during an balloon inflation procedure, an "emergency deflation" button may be provided as part of display screen 26 or on operator control 60, as examples, to allow the operator to quickly access an emergency deflation memory profile.

Fluid pump 40 is used to deliver fluid at desired pressure and flow rates for fluid injection and inflation procedures. Accordingly, fluid pump 40 is used as a fluid injector and a fluid inflator, but may also perform aspiration and depressurizing functions in system 10. Fluid pump 40 may have several different configurations, but is typically a syringe pump with a moving piston and drive powered by an electric motor that can easily achieve the pressures required for angioplasty and the flow rates needed for angiography. A suitable syringe pump or injector is disclosed in U.S. patent application Ser. No. 10/818,477, filed Apr. 5, 2004 and entitled "Fluid Injection Apparatus with Front Load Pressure Jacket, Syringe Holder, and Light Illumination", the disclosure of which is incorporated by reference in its entirety. Another possible configuration of fluid pump 40 is as a gear pump driven by an electric motor, such as a pump disclosed in U.S. patent application Ser. No. 11/403,119, filed Apr. 12, 2006 and entitled "Fluid Delivery System with Pump Cassette", incorporated herein by reference in its entirety. Other alternatives are also possible, including a pressurized chamber such as a syringe, compressed bag, or collapsible container driven by a spring, pneumatic, hydraulic device, or hydraulic pump.

Contrast used for fluid injection procedures is typically diluted for use in balloon inflation during angioplasty procedures. Low concentration contrast is typically diluted 1:1 or more with saline solution so that the combined fluid has a lower viscosity than contrast alone. Greater dilutions are used for larger balloons since the greater balloon diameter gives the same ratio density as a smaller diameter using lower media concentration. Use of diluted media allows for easier balloon priming and quicker deflation time if needed, since lower viscosity fluid flows more easily within the catheter lumen and the fluid mixture has a lower surface tension, decreasing the chance for trapped air bubbles.

Contrast injections are often performed during balloon inflation procedures to guide the operator. System 10, as discussed herein in connection with FIGS. 12-14, may comprise multiple fluid pumps or injectors 40 each drawing from separate fluid reservoirs that will allow injection of different mixes of fluids as desired. For example, system 10 could comprise two fluid pumps 40 with one fluid pump 40 dedicated to supplying pure contrast during an injection procedure and a second fluid pump 40 adapted to mix contrast and saline to a desired mixture level for use during a balloon inflation procedure or access a pre-mixed supply of contrast and saline. As an alternative to two fluid pumps 40, a single fluid pump 40 could be provided with appropriate connections to two fluid supplies, such as contrast and saline, and which is adapted to quickly convert between a fluid injection mode (e.g., pure contrast) and a fluid inflation mode (e.g., contrast-saline mixture). A dual fluid pump 40 configuration is currently preferred as a "contrast only" fluid injection supply could always be maintained and be ready for use in a fluid injection procedure. Additionally, the second fluid pump 40 could be associated with a pre-mixed or diluted supply of contrast, or a syringe associated with the second fluid pump 40 could be appropriately loaded with a mixture of contrast and saline by drawing from a contrast supply and a saline supply. Accordingly, a dual fluid pump 40 configuration allows for fast changes between fluid injection and inflation modes since the operator could access a pre-diluted supply of inflation contrast or could mix the contrast, and both a diluted and an undiluted output are both available for delivery to a patient. The dual reservoir/pump approach also offers the advantage of allowing the operator to use a different lower cost ionic contrast diluted with saline for balloon inflation and more expensive non-ionic contrast for injections which causes fewer side effects for the patient.

Fluid parameter feedback device 50 generally refers to sensors used to gather displacement (e.g., volume, fluid flow rate, and fluid acceleration) and/or pressure information from fluid path 70 and provide such input to pump controller 30, and optionally operator control 60 so that this information may be used as continuous feedback to the operator. Displacement (e.g., volume) feedback may be available directly at pump controller 30 based on volume command information in pump controller 30. Feedback may also come from a position sensor measurement of displacement of fluid pump 40, such as a potentiometer, optical encoder, LVDT, linear capacitive array, or other position sensing transducer that is attached to the pump drive mechanism. Volume or flow feedback may also be derived from fluid path 70 from a directly coupled flow sensor. An electronic integrator circuit associated with pump controller 30 can process the flow signal to derive displacement (e.g., volume) information.

In angiographic procedures, high feedback accuracy is not required (±50 psi or more), as pressure is only limited based upon the desire not to exceed the pressure limits of the components of fluid path 70 (e.g., connector tubing, connectors, transducers or catheters, etc). The pressure developed by fluid pump 40 may be estimated by the amount of current provided to the pump motor or actuator using the predetermined torque or force constant ($K_T$) of the motor or other actuator. As the current to the actuator increases, the force or pressure developed within fluid path 70 will increase by a corresponding amount.

Figure 2B:
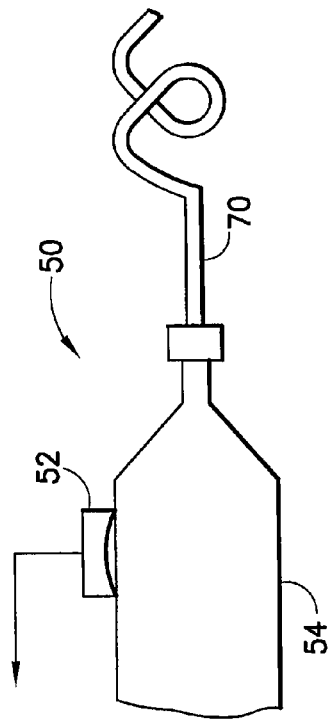
FIGS. 2A-2D are schematic views showing respective locations for associating a pressure sensor with a syringe used in the fluid injection and inflation system identified in block form in FIG. 1.
Figure 2A:
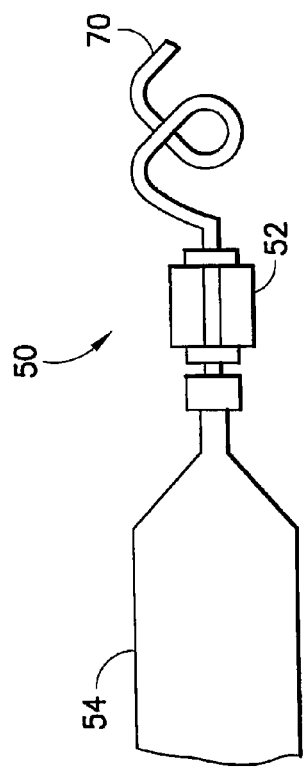
Figure 2D:
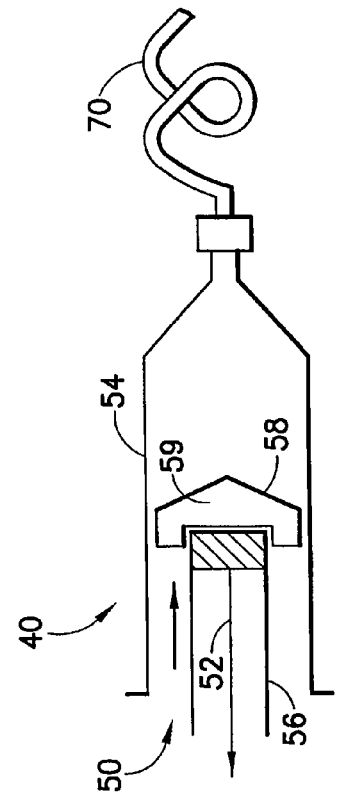
Figure 2C:
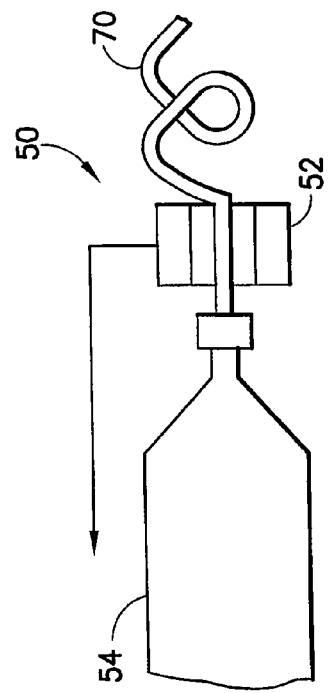

Referring to FIGS. 2A-2C, another feedback method uses direct measurement of pressure by placing a pressure sensor 52 at one or more location in fluid path 70. For example, a pressure sensor (not shown) could be placed at the end of the fluid delivery catheter which would provide direct information on the pressure within the blood vessel. In FIG. 2A, pressure sensor 52 is disposable and attached in-line with fluid path 70. This arrangement has the advantage of greater accuracy than the actuator current sensing technique described previously. Since pressure sensor 52 in FIG. 2A is part of fluid path 70, both pressure sensor 52 and fluid path 70 are desirably biocompatible and sterile before use. FIG. 2B illustrates a pressure sensor 52 schematically associated with a syringe 54 which may be actuated/operated by fluid pump 40. Pressure sensor 52 may be integrated directly into syringe 54, or into the wall of a disposable chamber of another type of pump or pressurizing device. When the disposable syringe 54 is removed from fluid pump 40, the entire pressure sensor 52 is also discarded. In another configuration, the syringe 54 contains an internal, disposable membrane that flexes when under pressure, which isolates the fluid from the actual pressure sensor 52 disposed on the outside of syringe 54.

FIG. 2C shows another configuration, wherein a sensing membrane is disposable but the pressure sensor 52 is reusable. In FIG. 2C, pressure sensor 52 is provided as a clip-on displacement or force sensor that attaches to fluid path 70 at the output of syringe 54, or fluid pump 40 generally. Pressure sensor 52 measures the expansion force or travel of fluid path 70 with pressure and provides a proportional output signal. As the fluid pressure increases within connector tubing forming, in part, fluid path 70, clip-on pressure sensor 52 measures the force communicated through the tube wall.

In yet another configuration shown in FIG. 2D, pressure sensor 52 is provided as part of fluid pump 40, wherein a portion of fluid pump 40, typically disposable syringe 54, operates as the flexible membrane. For example, pressure sensor 52 may be located at the interface between a piston 56 and a syringe plunger 58. Such an arrangement is disclosed in U.S. Pat. No. 5,808,203 to Nolan et al., the disclosure of which is incorporated herein by reference in its entirety. Pressure sensor 52 could measure the force applied against syringe plunger 58 when the fluid portion of system 10 develops pressure. The additional friction forces of syringe plunger 58 against the internal side wall of syringe 54 must be subtracted to derive an accurate measurement of fluid pressure. Pressure sensor 52 could also be coupled to the fluid pressure by using a portion of plunger cover 59 of syringe plunger 58 as a flexible membrane, since plunger cover 59 is typically formed of a resilient material and in direct contact with fluid path 70. As the pressure in syringe 54 increases, flexible plunger cover 59, due to its direct contact with the fluid pressure, would move or deform. This movement is sensed and translated into a corresponding fluid pressure value. In this specific embodiment, syringe friction does not need to be accounted for as it is not part of the measurement.

Operator control 60 is used to continuously, periodically (e.g., discretely), or rapidly and regularly, provide fluid parameter information to the operator during the course of a fluid injection or inflation procedure, and to continuously accept commands from the operator to control the fluid injection or inflation. The continuous feedback to the operator may be audio, visual, tactile or some combination of all three stimuli in nature. Examples of audible feedback include, but are not limited to: (1) a tone of increasing pitch or loudness with pressure; (2) variable rate clicks with pressure or flow rate; or (3) even voice announcements when discrete pressures or flow rates have been reached. Visual feedback could consist of real-time pressure, volume, or flow rate information on numeric displays, a bar graph, a strip chart, a variable brightness display, or a variable rate flashing display where the rate corresponds to a fluid parameter, or even an X-Y graph of pressure vs. displacement. An X-Y graph or other display of inflation pressure vs. volume may also be used as a source of useful diagnostic and clinical information on lesion compliance.

As indicated, continuous feedback to the operator may also be tactile in nature. One desirable embodiment of operator control 60 is as a hand controller 62, wherein displacement of a control member or actuator 64 provides a proportional input/command to the pump controller 30. Hand controller 62 typically comprises a member such as a motor, brake, or solenoid that is attached to the control member 64 and varies the amount of force required by the operator to move the control member 64. For example, a balloon inflation procedure may be controlled by the movement of control member 64 in the form of a plunger into the hand controller 62. As the plunger is depressed, fluid pump 40 will provide increasing fluid pressure. However, as fluid pressure increases in fluid path 70 as the plunger is depressed, the amount of force required by the operator to depress the plunger also increases, due to additional friction or opposing force generated by the member disposed within hand controller 62. Accordingly, the operator is able to have the tactile feel that they are physically controlling the fluid injection or inflation directly, much like using a hand syringe. It is also possible for the operator to selectively engage and disengage the tactile feedback capability if desired, as well as adjust the amount (e.g., scale) of feedback to suit the individual operator. If desired, control member 64 may be provided as a dual-trigger arrangement wherein one trigger lever would operate the fluid injection mode and the second trigger lever would operate the fluid inflation mode, thus allowing the operator to switch instantaneously between injection and inflation. Alternatively, hand controller 62 may be provided with a "joy-stick" control member 64 which may be adapted to toggle between fluid injection and inflation modes.

FIGS. 3A and 3B show an electromechanical tactile feedback hand control device 62 that is also suitable for use in system 10. Hand controller 62 shown in FIGS. 3A and 3B is a generally syringe-shaped structure and is operated by pushing a plunger/piston rod forming control member 64 into a syringe body 65. A potentiometer 66 is attached to a lead screw 67 and is used to measure the linear travel of plunger (e.g., control member) 64 disposed in syringe body 65. An electromechanical brake 68 is also connected to lead screw 67 to serve as the member that provides tactile feedback to the operator. A signal proportional to some fluid parameter, typically fluid pressure, is amplified and applied to brake 68, which generates a force (e.g., additional friction) against the operator's push. Electrical signals that indicate position and the feedback to the hand controller 62 are communicated to system 10 through a multi-conductor cable 69. FIG. 4 is a flow diagram/schematic of the control of fluid pump 40 in system 10 afforded by hand controller 62 and pump controller 30.

In addition to the foregoing increasing tactile resistance embodiments, other feedback methods are possible operator control 60 and hand controller 62 in accordance with the present invention. In another configuration, the force applied by the operator on hand controller 62 is used to generate a pressure command for pump controller 30, and the feedback takes the form of a displacement of control member 64 of hand controller 62. The control ratio, or proportional amount of tactile feedback to some system parameter in either case may be made adjustable continuously or in discrete steps to satisfy the operator's preference. Control member 64 displacement or actuation force may be used to control fluid delivery pressure, volume or flow rate, etc.

The full travel of control member 64 of hand controller 62 may be set to correspond to different delivery volumes, pressures, or flow rates depending on operator preference. In a volume control mode, if the "stroke" of control member 64 is set to be a fractional amount of the capacity of fluid pump 40, multiple fluid injections may be performed by returning control member 64 to its start position and then repeating the stroke. In another embodiment, fluid pump 40 may be bi-directional and made to reverse a proportional amount when control member 64 is returned to the beginning of its stroke. This allows the operator to control system 10 so as to inject as well as aspirate fluid. The ability to aspirate fluid is particularly helpful during set-up of fluid path 70, provided fluid path 70 is visibly clear so that system 10 may be checked for air bubbles after making fluid path 70 connections. In another example, reverse motion of fluid pump 40 is an indication that a syringe typically associated with fluid pump 40 should be refilled.

Various modes are also possible for hand controller 62 when combined with the programmed settings from operator interface 20. In one mode, control member 64 of hand controller 62 continues to travel when a pressure condition limit occurs. Typically, a pressure limit condition occurs when the pressure in fluid path 70 exceeds a preprogrammed desired maximum pressure. In another mode, control member 64 stops travel completely when a pressure limit occurs. This communicates to the operator that a pressure limit condition has been reached. In another mode, it is possible to vibrate or oscillate control member 64 about some set-point to indicate that a pressure limit has occurred, a preprogrammed pressure milestone has been reached, or that the remaining volume available for delivery is below some minimum.

Operator control 60 may include a pressure control mode for use in balloon inflation applications such as angioplasty, valvuloplasty, stent deployment, balloon-assisted drug delivery, balloon occlusion thrombectomy, or any other inflation application, and provided the operator with the ability to hold a given pressure. This provides the operator the ability to operate operator control 60 until a the desired pressure is reached, then activate a switch on operator control 60 that would cause pump controller 30 to hold and maintain a given pressure. This would allow for "hands-free" operation, once the fluid inflation has started. Similarly, a switch could be provided on operator control 60 that allows the user to immediately and quickly deflate the balloon in the case of a problem such as patient angina, vessel dissection, or incorrect balloon placement. In addition to switches and controls for these features, some of the operator interface 20 controls and displays could reside or be duplicated on operator control 60 for ease of access and use.

In addition to the hand controller 62 embodiment of operator control 60 described previously, other physical embodiments for operator control 60 are possible. For example, as indicated previously in connection with FIGS. 3A and 3B, operator control 60 may be shaped like a syringe. Alternatively, operator control 60 may be in the form of a pistol grip like a caulking gun, or be shaped like a box that is mounted to the side of the procedure table, or even as a foot pedal control 60' for positioning under an examination table, as specifically shown in FIGS. 5-7. It is believed that the most natural embodiment for operator control 60 is as a control unit that fits in the operator's hand. Such a control unit may have a variety of shapes and different actuation mechanisms and associated operator motions. For example, control member 64 could be a plunger that is depressed as described previously. Other examples of suitable actuation mechanisms include a shaft with linear travel that is pushed, a lever that is moved, a rotating knob that is twisted, a rotating knob that ratchets, a screw-in-shaft that is twisted and/or pushed, or even a button that is depressed. Also, the hand control could be directly wired to one or more of the other components in system 10, or could be a battery operated device that is wirelessly coupled to the components of system 10. Finally, operator control 60 may use fluid power to provide the tactile feedback force to control member 64. Pressurized fluid from fluid pump 40 connected to a hydraulic piston or drive may be used to provide the requisite tactile feedback force.

As hand controller 62 is likely to come into close proximity to the patient undergoing an injection procedure or a balloon inflation procedure, hand controller 62 should be sterile prior to use. Sterility may be ensured in a number of ways. For example, the entire unit could be cold sterilizable and resterilized after each use. Additionally, hand controller 62 could have some type of disposable sterile cover that is used with it such as a "steri-bag". Further, the housing of hand controller 62 could be disposable while the internal components of hand controller 62 are reused. The non-sterile internal components would be retained for future procedures. Moreover, the entire hand controller 62 could be a disposable item. It will be appreciated that any cable associated with hand controller 62 and operating within the sterile field should also have a sterile cover or be provided in a sterile state and be discarded after each procedure. Finally, it will be appreciated that a handheld operator control 60 provides a distinct advantage to an operator in that the operator is able to keep his or her hands away from the radiation field during imaging.

Fluid path 70 is used to deliver the fluid output from fluid pump 40 to a catheter inserted intravenously into a patient. Fluid path 70 is comprised of connecting tubing, suitable valves, and manifolds for delivering fluid output from fluid pump 40 to the catheter. Fluid output from fluid pump 40 may also be provided directly to the input of a multi-port manifold. Fluid path 70 may also include a stopcock and waste bag for draining fluid and venting air. For balloon inflations, the fluid delivery output of fluid pump 40 is connected via connector tubing directly to the inflation lumen of a balloon catheter (See FIGS. 15-18). As system 10 is typically adapted to both inject fluid into a patient via a catheter and inflate a balloon associated with the same or a different catheter, it is important for the operator to identify and use the correct catheter port for fluid injection and the correct catheter port for fluid inflation. For example, if an operator accidentally uses the fluid injection mode to inject fluid into the balloon lumen of the catheter at a high pressure setting, the balloon may burst. It is envisioned to use different markings or different connectors for the fluid injection and inflation outputs of fluid pump 40. For example, it is possible to identify the connected disposable devices through machine readable markings or tags, such as bar codes, electronic labels, optical markings, physical indicia, RFID tags, and the like. If an incorrect connection is made, this error may be made to register on operator interface 20 and appropriate action could be automatically implemented such as the operator interface 20 sending a signal to operator control 60 disabling the operator control 60 and preventing the operator from initiating any type of procedure.

Figure 11:
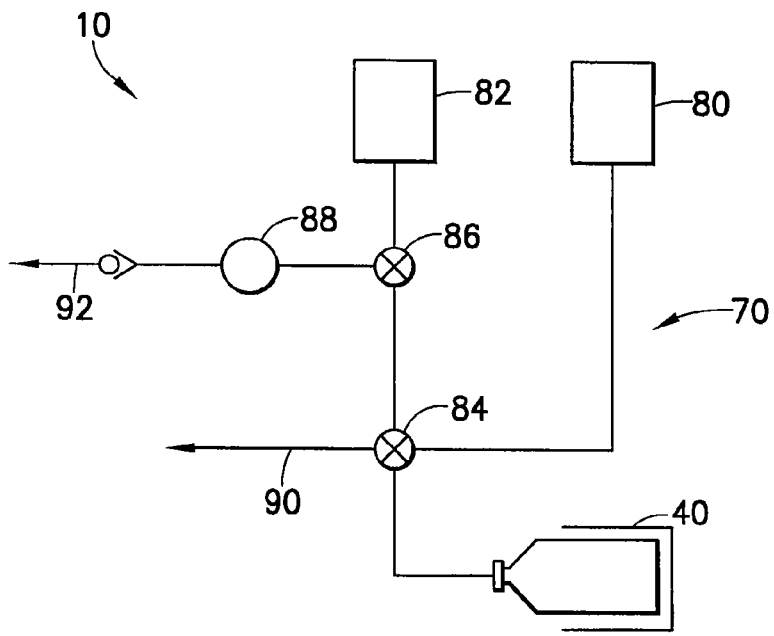
FIG. 11 is a fluid path schematic diagram of the fluid injection and inflation system.

FIG. 11 is a fluid path diagram showing system 10 associated with two sources of fluid, typically contrast and saline, for delivery to a patient via a catheter (not shown). For simplicity, system 10 is illustrated with the control components of system 10 omitted, namely operator interface 20, pump controller 30, fluid parameter feedback device 50, and operator control 60. Accordingly, FIG. 11 generally illustrates how fluid path 70 associates fluid pump 40 with a contrast source 80 and a saline source 82, or any two desired fluids, and delivers these fluids, either separately or as a mixture, to a patient. Fluid path 70 includes a first fluid control valve 84 positioned in fluid path 70 for selectively associating fluid pump 40 with contrast source 80 and saline source 82. As shown in FIG. 11, fluid path 70 further comprises a second fluid control valve 86 for isolating saline source 82 from fluid pump 40 and associating saline source 82 with the catheter or fluid pump 40. Such fluid control valves 84, 86 may be manually operated or operated automatically, as are any of the fluid control valves described hereinafter. A peristaltic pump 88 or other suitable pump apparatus is associated with second fluid control valve 86 to supply saline as required to the catheter for flushing operations. Accordingly, fluid path 70 generally comprises a first or high pressure output 90 and a second or lower pressure output 92 to the catheter inserted into the patient. As discussed previously, the catheter inserted into the patient is typically a multi-lumen catheter having at least one port/lumen associated with first high pressure output 90 and at least one port/lumen associated with lower pressure output 92. Alternatively, two catheters may be inserted into the patient and be respectively associated with the first high pressure output 90 and lower pressure output 92. Moreover, outputs 90, 92 may connected to a single lumen catheter so that contrast and saline are delivered to one lumen in the catheter. It will be appreciated that lower pressure output 92 should be protected in some manner from the higher pressure present in first high pressure output 90, for example, by a check valve as illustrated, or a suitable pressure isolation valve.

In operation, fluid pump 40 may be used to supply contrast alone or a mixture of contrast and saline to the patient via a catheter (not shown). If contrast alone is required, as in a fluid injection procedure for angiography, first fluid control valve 84 is operated to allow fluid communication with contrast source 80. Fluid pump 40 may be operated to fill a disposable syringe, typically associated with fluid pump 40 as described previously, with contrast from contrast source 80 and then aspirate any air that may be in fluid path 70 into contrast source 80. As fluid pump 40 is typically a syringe pump, fluid pump 40 will be referred to hereinafter as "syringe pump 40" for convenience. Once syringe pump 40 is ready for a fluid injection procedure, first fluid control valve 84 is operated to place syringe pump 40 in fluid communication with first high pressure output 90 and further isolates saline source 82 and peristaltic pump 88 from the output from syringe pump 40. Syringe pump 40 may be operated to inject contrast under high pressure via first high pressure output 90 to a fluid injection lumen of the catheter. Saline is available via lower pressure output 92 via the same or another fluid injection lumen of the catheter. It will be appreciated that operator interface 20, pump controller 30, fluid parameter feedback device 50, and operator control 60 all interface with syringe pump 40 to control operation of syringe pump 40 in the manner described previously, as will be the case with other embodiments of system 10 described hereinafter in connection with FIGS. 12-14. In FIGS. 11-14, it is generally desired to have saline ready to follow any fluid injection procedure involving contrast such that the saline is injected through one or more fluid injection lumens in the catheter to clear contrast in the catheter and/or blood vessel.

In addition to delivering "pure" contrast to first high pressure output 90, syringe pump 40 may be loaded with a mixture of contrast and saline for use in a balloon inflation procedure using the catheter. In this operational variation, first high pressure output 90 may connected (e.g., switched) to a balloon inflation lumen of the catheter and the first and second fluid control valves 84, 86 may be operated to allow fluid communication between syringe pump 40 and both contrast source 80 and saline source 82, while second fluid control valve 86 further isolates peristaltic pump 88 from saline source 82. Accordingly, syringe pump 40 may be operated to draw fluid simultaneously from contrast source 80 and saline source 82. Mixing of contrast and saline may occur in the tubing forming fluid path 70, in first fluid control valve 86, or in a designated mixing apparatus (not shown) provided in fluid path 70, or even in syringe pump 40 itself. It will also be understood that first and second fluid control valves 84, 86 may be sequentially operated to sequentially draw contrast and saline from respective sources 80, 82. In this type of draw, mixing of contrast and saline will typically occur in syringe pump 40. Once an appropriate mixture of contrast and saline is provided in syringe pump 40, syringe pump 40 is ready to supply the mixture for a balloon inflation procedure, and system 10 is generally operated as discussed previously. Accordingly, first fluid control valve 84 is operated to place syringe pump 40 in fluid communication with first high pressure output 90, and second fluid control valve 86 is operable to isolate saline source 82 and peristaltic pump 88 from the output from syringe pump 40. Syringe pump 40 may be operated to inject the mixture of contrast and saline under pressure via first high pressure output 90 to the balloon inflation lumen of the catheter. Lower pressure output 92 may provide, for example, saline through a fluid injection lumen in the catheter.

Figure 12:
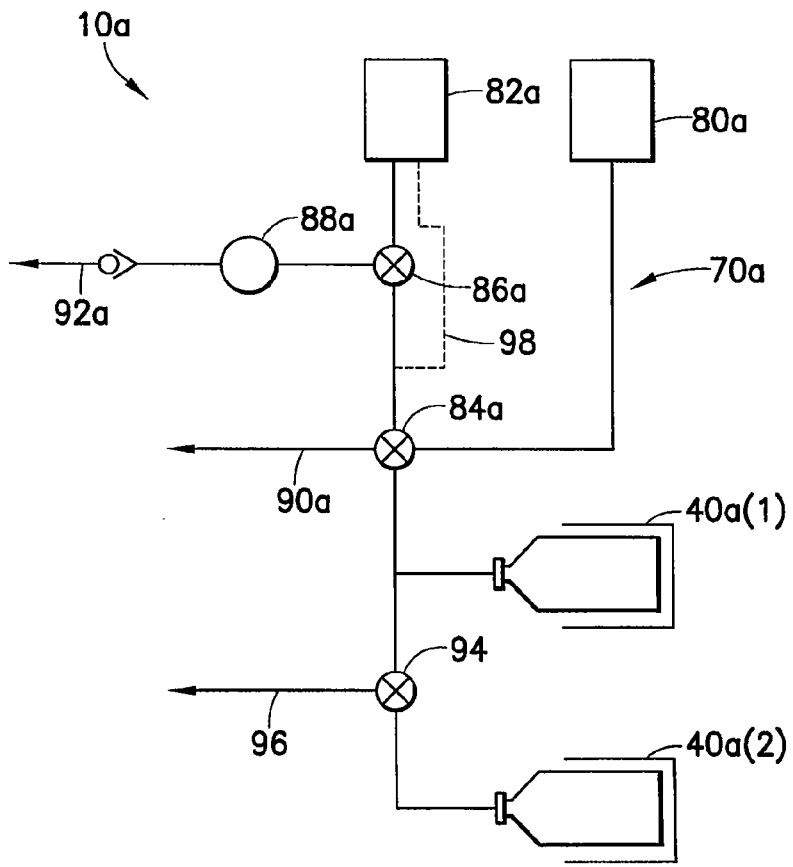
FIG. 12 is a fluid path schematic diagram showing the fluid injection and inflation system with two fluid delivery devices/injectors.

FIG. 12 illustrates a modification to system 10 shown in FIG. 11. System 10a shown in FIG. 12 further comprises a second syringe pump identified with reference numeral 40a(2) while first syringe pump is identified with reference numeral 40a(1). In system 10a, second syringe pump 40a(2) augments first syringe pump 40a(1) present in system 10, and is generally intended to be a dedicated supplier of contrast for fluid injection procedures. Accordingly, saline is not typically loaded into second syringe pump 40a(2) and second syringe pump 40a(2) is intended for repeated and often intermittent high pressure injection of contrast into the patient such as often occurs during angiography procedures. Other than the addition of second syringe pump 40a(2), system 10a shown in FIG. 12 includes the same basic components as system 10 shown in FIG. 11.

Second syringe pump 40a(2) is connected to the remainder of system 10a via a third fluid control valve 94. Output from second syringe pump 40a(2) is passed to a second high pressure output 96 via third fluid control valve 94. Second high pressure output 96 is connected either to its own fluid injection lumen in the catheter or to a fluid injection lumen to which lower pressure output 92a (e.g., saline) is connected, with appropriate protections placed in-line in lower pressure output 92a as indicated previously. The use of two syringe pumps 40a(1), 40a(2) enables the operator maintain a clean or pure supply of contrast for injection into the patient which is typically used during balloon inflation procedures to guide the operator. First syringe pump 40a(1) may be loaded with a mixture of contrast and saline in the manner described previously, or any two fluids, to allow balloon inflation procedures to be conducted via a balloon inflation lumen in the catheter. Control valves 86a, 94 are operated to isolate the output of syringe pump 40a(1) to conduct the balloon inflation (and/or deflation) procedure. Saline alone or in combination with contrast is available via low pressure output 92a (and peristaltic pump 88a) and second high pressure output 96 (and syringe pump 40a(2)), as desired by the operator through the fluid injection lumen in the catheter again with suitable pressure protection in place for the low pressure side of system 10a.

When it is desired to provide an injection of contrast alone into the patient, first and third fluid control valves 84a, 94 may be operated to place second syringe pump 40a(2) in fluid communication with contrast source 80a. Syringe pump 40a(2) may then be operated to draw a fill of contrast. Once second syringe pump 40a(2) is filled with a dose or fill of contrast and any air in the second syringe pump 40a(2) is aspirated. First and third fluid control valves 84a, 94 may be operated to place second syringe pump 40a(2) in fluid communication with the fluid injection lumen of the catheter via second high pressure output 96. Second fluid control valve 94 is used to isolate the output of second syringe pump 40a(2) during any injection procedure. Second syringe pump 40a(2) may then be operated to inject the contrast into the patient. First syringe pump 40a(1) is available as a balloon inflator in the manner described previously in connection with system 10 of FIG. 11 and may be connected or remain dedicated to a balloon inflation lumen of the catheter.

While systems 10, 10a were described with reference to contrast and saline as the two fluids for using in systems 10, 10a, it will be appreciated that systems 10, 10a may be operable with any two desired fluids. For example, in system 10 of FIG. 11, it may be desirable to use syringe pump 40 as a drug delivery vehicle. Accordingly, contrast source 80 may be replaced by a drug source, which can be injected under pressure into the patient using syringe pump 40. Drug source fluid may be mixed with saline in the manner described previously in connection with contrast. Dashed line 98 in FIG. 12 identifies that second fluid control valve 86a may be bypassed entirely so that saline may be directly drawn from saline source 82a by first and second syringe pumps 40a(1), 40a(2).

Often, it may be useful to allow for rapid deflation and aspiration or withdrawal of fluid when a sudden pressure decrease is detected in order to remove debris or particulate matter that is dislodged during the angioplasty procedure. If this occurs, first syringe pump 40a(1) may be immediately turned off by a master system control associated with system 10a and second syringe pump 40a(2) actuated in a reverse mode whereby an dislodged debris or particulate matter is suctioned into the fluid injection lumen of the catheter, for example, preventing this material from causing possible injury to the patient. Such an emergency mode may be provided as an emergency switch on a handcontroller associated with system 10a, or with the operator interface 20a (not shown) associated with system 10a. The foregoing concept may be applied to any of the systems 10 described in this disclosure and is not limited to the specific arrangement shown in FIG. 12.

Figure 13:
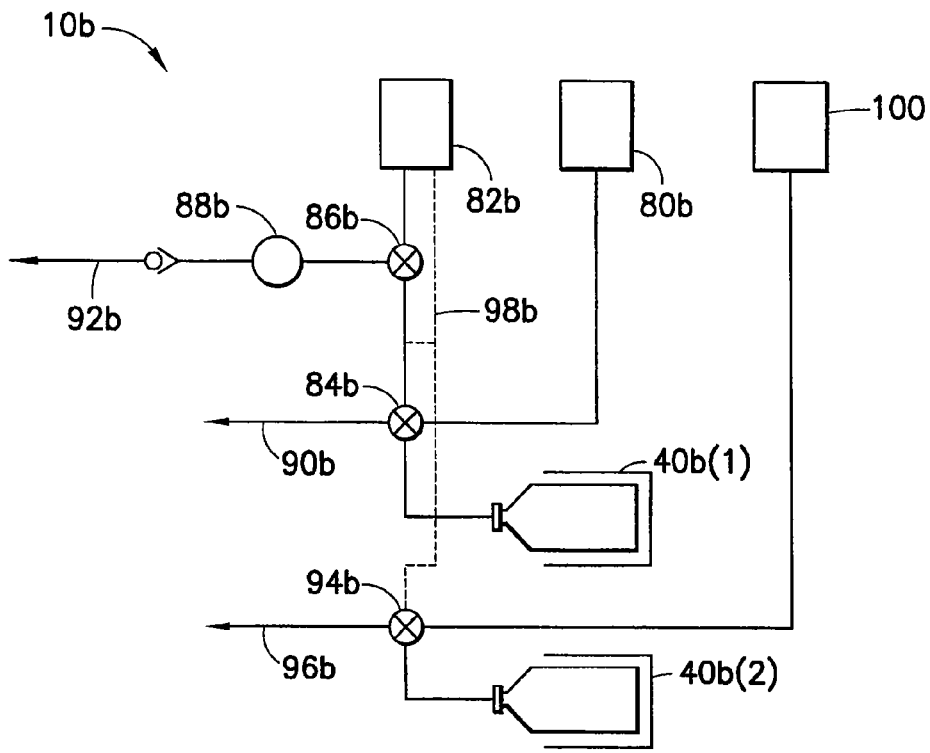
FIG. 13 is a fluid path schematic diagram showing the fluid injection and inflation system with two fluid delivery devices/injectors and multiple sources of fluid for delivery to a patient.
Figure 14:
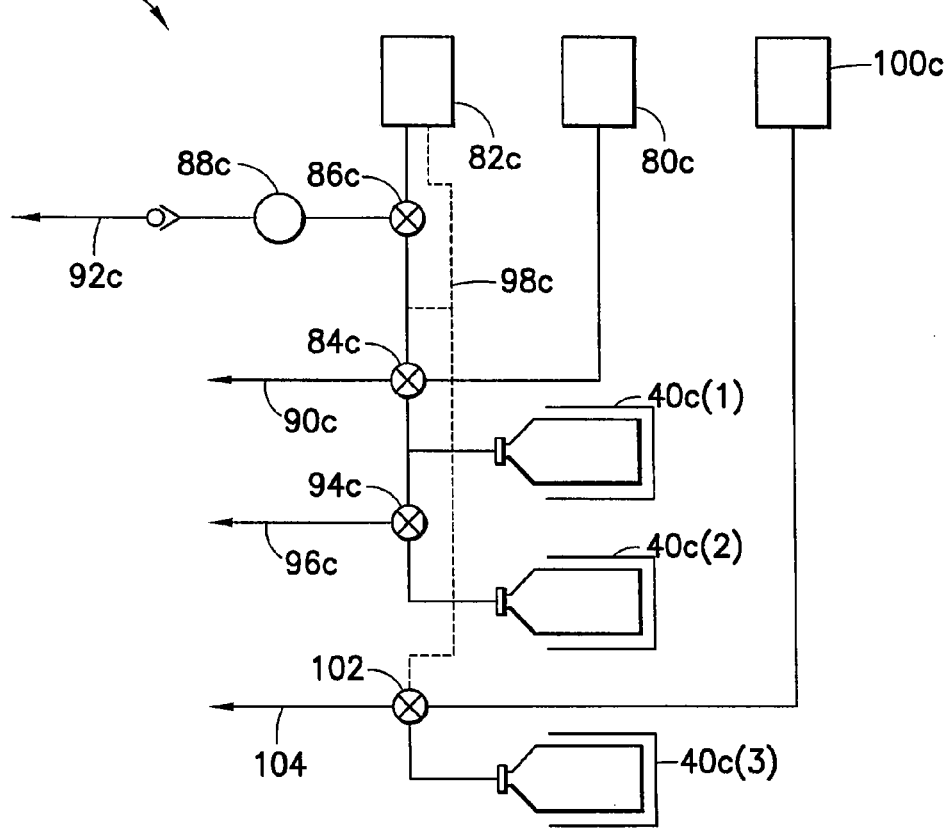
FIG. 14 is a fluid path schematic diagram showing the fluid injection and inflation system with multiple fluid delivery devices/injectors and multiple sources of fluid for delivery to a patient.

FIGS. 13 and 14 build upon the foregoing concept of supplying a third fluid to a patient, such as a drug containing liquid, using system 10. System 10b illustrated in FIG. 13 comprises the same basic components as system 10 shown in FIG. 11 but adds second syringe pump 40b(2) for the purpose of supplying a third fluid, such as a drug-containing liquid, to the patient via the catheter. The third fluid may be a drug-containing fluid from a drug source 100. As discussed previously in connection with FIG. 11, first syringe pump 40b(1) may be used to supply contrast alone or a mixture of contrast and saline via first high pressure output 90b to the catheter. Again, saline is continuously available from saline source 82b via second fluid control valve 86b and peristaltic pump 88b for delivery to lower pressure output 92b, typically connected to the same fluid injection lumen as first high pressure output 90b in the contrast injection mode. Second syringe pump 40b(2) is connected via third fluid control valve 94b to drug source 100 and second high pressure output 96b. When it is desired by the operator of system 10b to supply the drug-containing fluid under pressure to the patient, third fluid control valve 94b may be operated to place second syringe pump 40b(2) in fluid communication with drug source 100. Syringe pump 40b(2) may then be operated to draw a fill of drug media. Once second syringe pump 40b(2) is filled with a dose or fill of drug media and any air in the second syringe pump 40b(2) is aspirated. Third fluid control valve 94b may be operated to place second syringe pump 40b(2) in fluid communication with a fluid injection lumen of the catheter via second high pressure output 96b, and first fluid control valve 94b isolates the remainder of system 10b from the output from second syringe pump 40b(2). Second syringe pump 40b(2) may then be operated to inject the drug media into the patient. While the third fluid source is described hereinabove as a drug-containing fluid, it will be appreciated that this third source of fluid may also be contrast so that second syringe pump 40b(2) comprises a dedicated source of contrast for injection into the patient, while first syringe pump 40b(1) is used or operated as a balloon inflator via first high pressure output 90b and the balloon inflation lumen of the catheter. Additionally, as this third source of contrast is fluidly separated from the other two sources, it may comprise more expensive non-ionic contrast than the contrast in contrast source 80b. Contrast in contrast source 80b may comprise lower cost ionic contrast which is diluted with saline from saline source 82b for balloon inflation procedures using first syringe pump 40b(1).

The operation of system 10c shown in FIG. 14 is analogous to the operation system 10a discussed hereinabove. System 10c incorporates the basic components of system 10a of FIG. 12, with the addition of a third syringe pump 40c(3) for the purpose of supplying a third fluid to the patient via the catheter. The third fluid may be a drug-containing fluid from a drug source 100c. As described previously in connection with FIG. 12, the use of two syringe pumps 40c(1), 40c(2) enables the operator maintain a clean supply of contrast from second syringe pump 40c(2) for fluid injection into the patient, while first syringe pump 40c(1) is available as a balloon inflator with a mixture of contrast and saline. Saline will again be continuously available via low pressure output 92c and peristaltic pump 88c and connected, typically, to the same fluid injection lumen of the catheter as the second high pressure output 96c. Third syringe pump 40c(3) is connected via a fourth fluid control valve 102 to drug media source 100c and a third high pressure output 104. As will be understood, lower pressure output 92c is connected to (e.g., in fluid communication with) one or both of high pressure outputs 96c, 104 via the fluid injection lumen(s) of the catheter, while first high pressure output 90c is connected or dedicated to the balloon inflation lumen of the catheter. When it is desired by the operator of system 10c to supply drug media under pressure to the patient, fourth fluid control valve 102 may be operated to place third syringe pump 40c(3) in fluid communication with drug source 100c. Third syringe pump 40c(3) may then be operated to draw a fill of drug media. Once third syringe pump 40c(3) is filled with a dose or fill of drug media and any air in the third syringe pump 40c(3) is aspirated, fourth fluid control valve 102 may be operated to place third syringe pump 40c(3) in fluid communication with a fluid injection lumen of the catheter via third high pressure output 104. Third syringe pump 40c(3) may then be operated to inject the drug media into the patient. Contrast alone or a mixture of contrast and saline may be delivered to the catheter from system 10c in the manner described previously in connection with FIG. 12.

Figure 15:
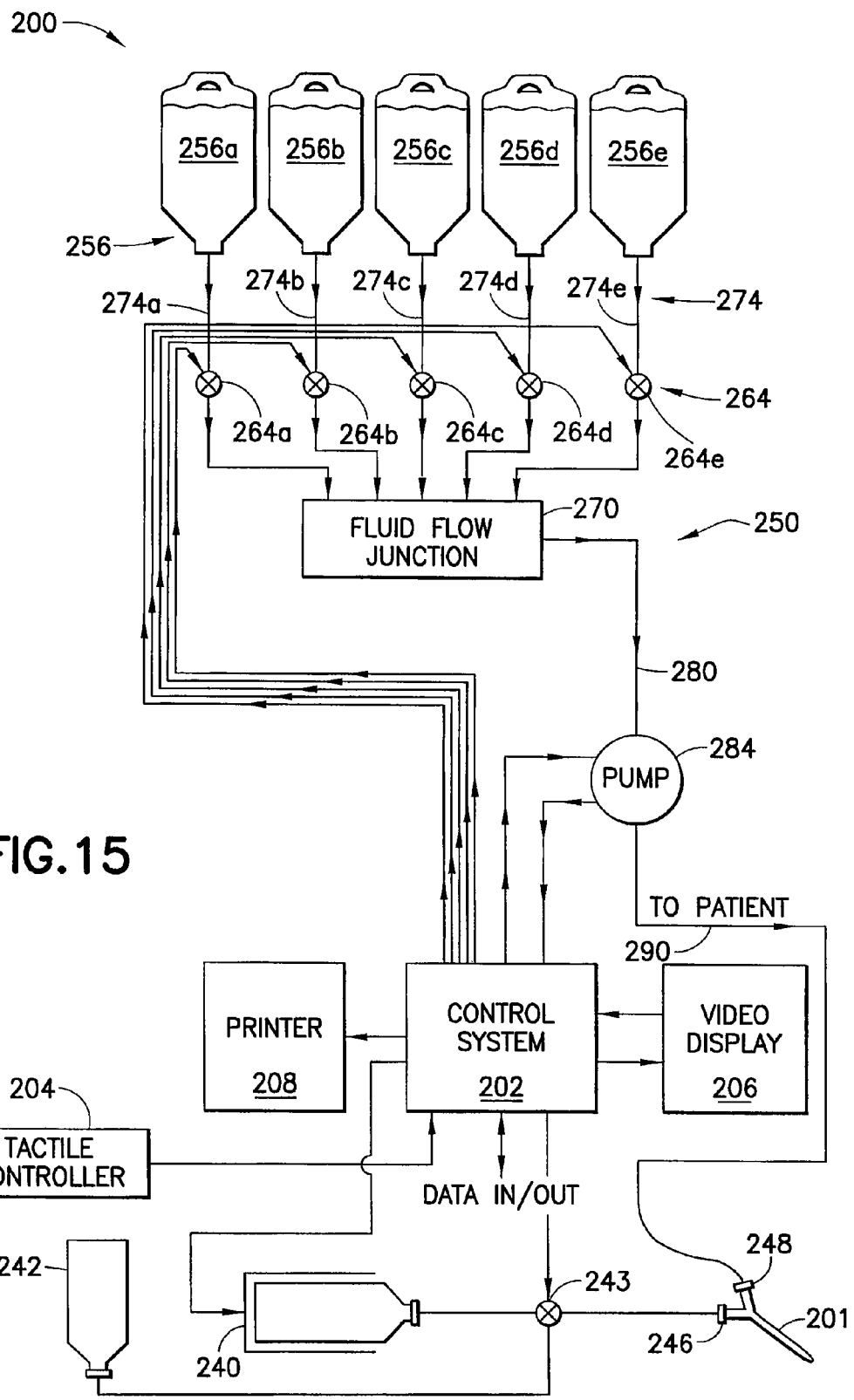
FIG. 15 is a schematic diagram of another embodiment of the fluid injection and inflation system wherein multiple fluids may be delivered to a patient by the system.

FIG. 15 further amplifies on the foregoing concept of supplying multiple distinct fluids to a patient while retaining an independent contrast injection capability and/or a balloon inflation capability. FIG. 15 is a schematic diagram of a system 200 in which multiple fluids may be provided to the patient via a catheter 201, while a separate contrast injection capability is retained. The fluids may be provided in pure form or mixed together in any desired combination and delivered under pressure to the patient, as discussed herein.

System 200 includes similar components to system 10 described previously. System 200 includes a control system 202 which may be considered to encompass the functionality of the operator interface 20, pump controller 30, and fluid parameter feedback device 50 of system 10 discussed previously. System 200 may further comprise a tactile controller 204 similar to operator control 60 described previously. A video (e.g., screen) display 206 and a printer 208 may also be provided in system 200 in a similar manner to system 10 described previously. Additionally, system 200 comprises a fluid pump 240 that is equivalent to syringe pump 40 described previously.

As indicated, system 200 generally combines the ability to supply multiple fluids, individually or in combination, with the ability to inject a ready source of contrast into the patient on operator demand. Accordingly, fluid/syringe pump 240 is associated with a dedicated supply or source 242 of contrast by a fluid control valve 243, also controlled by control system 202. The output of syringe pump 240 is associated with a high or higher pressure, fluid injection lumen 246 of catheter 201 for supplying the contrast under high pressure to the patient. Catheter 201 typically further comprises a low pressure or lower pressure lumen 248 for delivering other fluids, such as drug containing liquids or saline to another (or same) fluid injection lumen in the catheter to the patient, or for balloon inflation purposes, provided a balloon and balloon inflation lumen is associated with catheter 201 as discussed herein.

System 200 further comprises a multi-fluid delivery apparatus 250 for delivering one or more additional fluids to the patient via catheter lumen 248. Fluid delivery apparatus 250 comprises a plurality of fluid sources 256a-256e each typically containing a distinct fluid for delivery to the patient. The fluid sources 256a-256e may respectively contain saline, contrast, and different drug media. Each fluid source 256a-256e is coupled via a corresponding flexible conduit 274a-274e through a corresponding fluid control valve 264a-264e to a fluid flow junction 270. Output line 280 from the fluid-flow junction 270 passes through a pump 284, such as a peristaltic pump or a fluid pump similar to syringe pump 240. Output from pump 284 via output fluid-flow conduit 290 is connected to catheter lumen 248 as shown in FIG. 15. Control system 202 is operatively connected to control valves 264a-264e, pump 284, and syringe pump 240 and fluid control valve 243 to control overall operation of system 200. A check valve may be provided in output fluid-flow conduit 290 to prevent fluid back up to pump 284.

As configured in FIG. 15, fluid delivery apparatus 250 may be controlled by control system 202 such that any one of fluid sources 256a-256e may be selected for delivery to the patient via fluid flow junction 270 and pump 284. Additionally, control system 202 may be used to select any combination of fluids from fluid sources 256a-256e by actuating the associated fluid control valves 264a-264e to supply the selected fluids from the accessed fluid sources 256a-256e to fluid flow junction 270. Fluid flow junction 270 may be a mixing apparatus adapted to mix the selected fluids together before the fluids are delivered under pressure to catheter lumen 248 by pump 284. For example, it may be desirable to access fluid sources 256b and 256c which may contain two different drugs and mix these fluids with saline from, for example, fluid source 256a. Control system 202 may actuate, via tactile controller 204, control valve 264a-264c associated with fluid sources 256a-256c to allow these fluids to flow into fluid flow junction 270, where they are mixed before being delivered to catheter 201 via pump 284. Alternatively, each of these fluids may be delivered sequentially to the patient via pump 284. It will be appreciated that two of fluid sources 256a-256e may be contrast and saline and pump 284 may itself be used an inflation device for a balloon associated with catheter 201. It is known that peristaltic pumps are capable of generating sufficient fluid pressure to be used in balloon inflation procedures.

Fluid delivery apparatus 250 is conventional in the art and a suitable example for this apparatus is disclosed in U.S. Pat. No. 4,925,444 to Orkin et al., discussed previously, and which is now incorporated herein by reference in its entirety. Other suitable examples of multifluid delivery systems are disclosed by U.S. Pat. Nos. 5,199,604 to Palmer et al. and 4,559,036 to Wunsch, both of which were discussed previously, and which are also incorporated herein by reference in their entirety. System 200 improves upon the multi-fluid delivery systems disclosed in the foregoing patents because syringe pump 240 remains dedicated for supplying contrast under pressure to the patient. Additionally, it will be understood that fluid delivery apparatus 250 may take the location of the drug-supplying second syringe pump 40b(2) in system 10b of FIG. 13 and the drug-supplying third syringe pump 40c(3) in system 10c of FIG. 14. Moreover, while not illustrated an additional syringe pump 240(2) may be provided in system 200 which may be dedicated as a balloon inflator and controlled by control system 202. Such a second syringe pump 240(2) may be associated with contrast source 242 and a source of saline (not shown) or one of fluid sources 256a-256e filled with saline.

Figure 18:
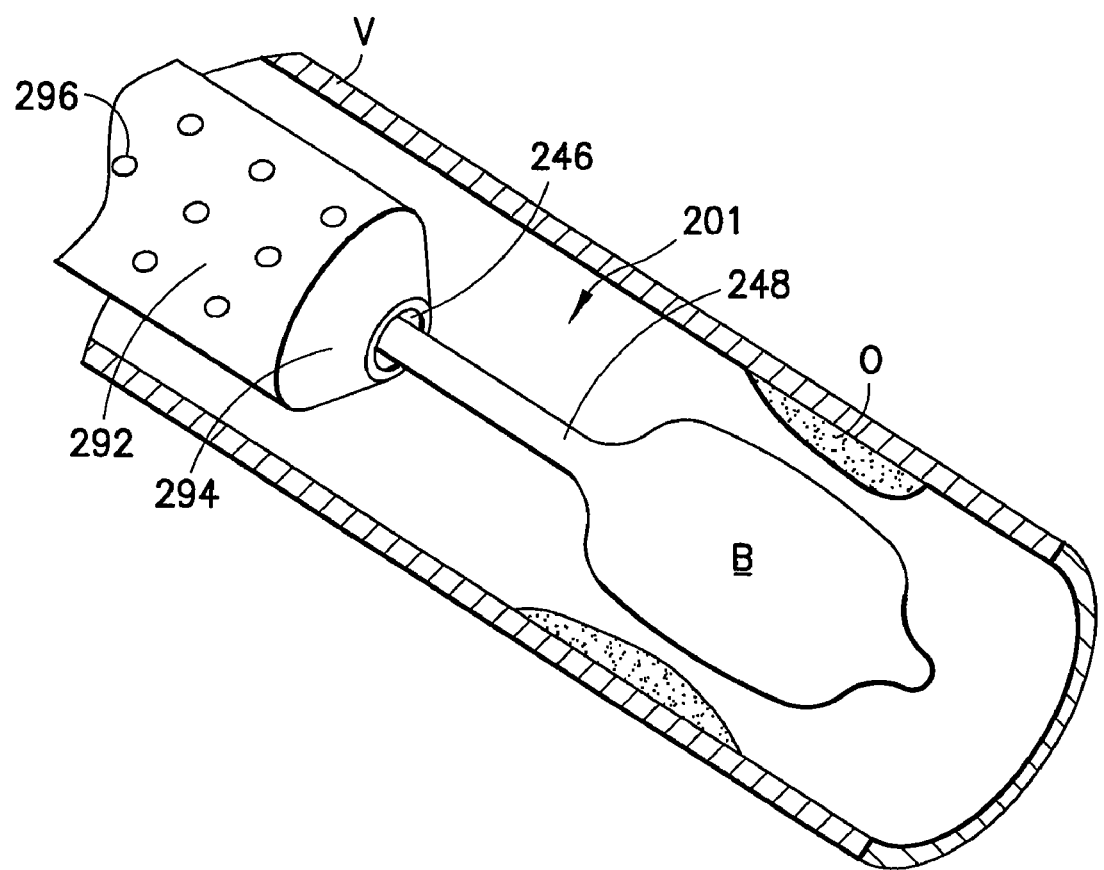
FIG. 18 is a cross-sectional and perspective view of a multiple lumen catheter for use with the various embodiments of the fluid injection and inflation system.

Referring briefly to FIG. 18, an exemplary catheter for two lumen catheter 201 for fluid injection and balloon inflation operations is shown indwelling in a blood vessel V. As shown in FIG. 18, a lumenal body 292 generally forming catheter 201 includes a distal end 294 which is inserted in the blood vessel V. As an example, catheter 201 may be used as an angioplasty device wherein a balloon B is inflated by system 200 (as described herein) to compress vessel occlusion O against the wall of blood vessel V. Lumenal body 292 defines inner or low pressure lumen 248 which is used to supply inflation fluid to balloon B. Such inflation fluid typically comprises a mixture of contrast and saline as described previously. In the context of system 200 shown in FIG. 15, low pressure lumen 248 comprises a balloon inflation lumen with pump 284 or a substitute second syringe pump 240(2) (not shown), or other pump device as disclosed in this disclosure, used an inflation device for balloon B associated with catheter 201. As described previously, it is known that peristaltic pumps are capable of generating sufficient fluid pressure to be used in balloon inflation procedures.

Lumenal body 292 further defines outer or high pressure lumen 246 which is coaxially disposed about inner lumen 248 and is used for fluid injection procedures (e.g., comprises a fluid injection lumen) wherein a medical fluid such as contrast is injected into blood vessel V. Such fluid injection procedures include the injection of contrast for angiographic diagnostic study of blood vessel V as one example. Lumenal body 292 may define a plurality of fluid delivery apertures 296 for the delivery of fluid along the length of lumenal body 292 or just along a portion thereof, for example, the portion of lumenal body 292 proximate of distal end 294. Such apertures 296 are only provided to allow fluid communication between the blood vessel interior and the outer lumen 246. The example of two lumen catheter 201 shown in FIG. 18 is exemplary of a multi-lumen catheter that may be used in any of the embodiments of system 10 set forth in this disclosure.

Figure 16:
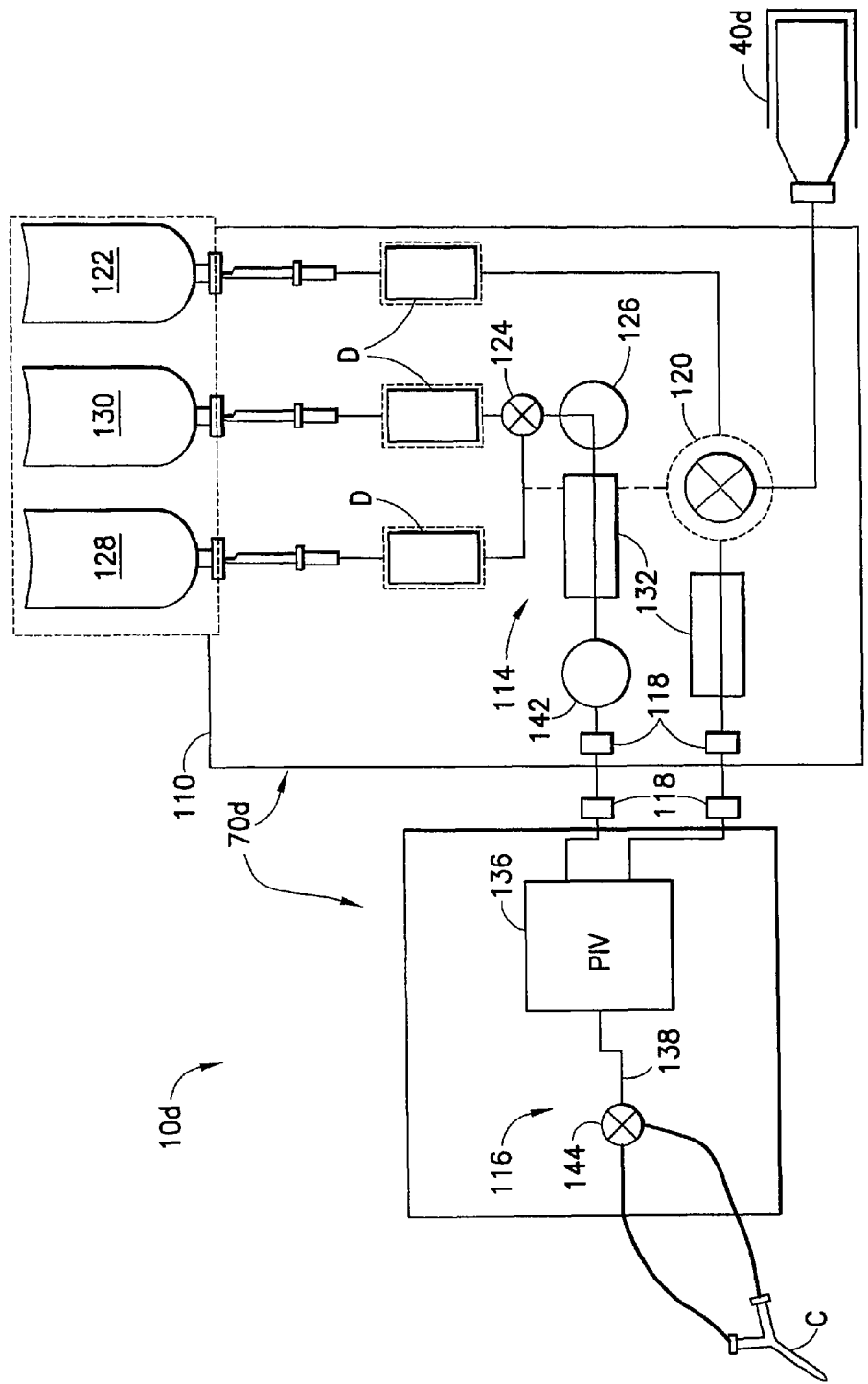
FIG. 16 is a schematic diagram of another embodiment of a fluid injection and inflation system for delivering fluids to a patient.

Referring now to FIG. 16, another embodiment of system 10d is illustrated. System 10d is generally analogous in configuration and operation to system 10b discussed previously in connection with FIG. 13. However, the various components of system 10d are disclosed in U.S. patent application Ser. No. 11/078,813, filed Apr. 16, 2004 and entitled "Fluid Delivery System, Fluid Control Device, and Methods Associated with the Fluid Delivery System", the disclosure of which is incorporated herein in its entirety by reference. System 10d generally comprises a fluid control module 110 for controlling delivery of fluid from multiple fluid sources to a patient via a catheter C, which is similar in construction to catheter 201 discussed previously in connection with FIG. 18, (e.g., comprises a higher pressure, fluid injection lumen and lower pressure, balloon inflation lumen). Fluid control module 110 may control operation of syringe pump 40 and the various control valves associated or supported on the fluid control module 110 (as described in application Ser. No. 11/078,813) to effect operation of system 10d. Thus, fluid control module 110 operates as a control unit for system 10d, taking the place of or operating as the pump controller 30 described previously. Suitable devices for use in place of operator interface 20, pressure/feedback device 50, and operator control 60 are described in foregoing application Ser. No. 11/078,813. System 10d further comprises a fluid injector in the form of a syringe pump 40d which is fluidly coupled to the catheter via fluid path 70d. Fluid path 70d is supported on fluid control module 110 which controls fluid flow through fluid path 70d to catheter. Typically, fluid path 70d comprises a reusable portion 114 supported by fluid control module 110 and a disposable portion 116 associated with the catheter. Reusable portion 114 and disposable portion 116 are connected by aseptic connectors 118.

Fluid control module 110 includes an automated fluid control valve 120 for connecting syringe pump 40d to a first fluid source 122, typically contrast. Fluid control module 110 further comprises a second automated fluid control valve 124 for associating a peristaltic pump 126 with a saline source 128 and/or a second contrast source 130. Fluid control valve 124 allows for delivery of a mixture of contrast and saline from sources 128, 130 or delivery of one liquid (e.g. contrast or saline) from sources 128, 130. It is often desirable to provide saline only for flushing operations involving catheter C which is permitted by fluid control valve 124 and pump 126. Drip chambers D may be associated with each fluid source 122, 128, 130. Air detectors 132 may be provided downstream of peristaltic pump 126 and first automated fluid control valve 120 to check for air in reusable portion 114 of fluid path 70d during operation of system 10d. The output from syringe pump 40d and the output from second automated fluid control valve 124 are respectively passed through a pressure isolation valve 136 for delivery to an output conduit 138 used to supply fluid to the catheter C.

In operation, system 10d may be used as both a balloon inflator or as a contrast injector as desired by an operator. In the balloon inflation mode, first automated fluid control valve 120 may be operated to isolate syringe pump 40d from pressure isolation valve 136. Second automated fluid control valve 124 may be operated to allow fluid from saline source 128 and secondary contrast source 130 to enter valve 124. The contrast from secondary contrast source 130 and saline from saline source 128 may mix within the tubing forming reusable fluid path portion 114 or second automated fluid control valve 124 may be adapted to mix these fluids. A mixing apparatus may be located upstream or downstream of valve 124 to also perform this mixing function if desired. Peristaltic pump 126 may then be used to supply the mixed fluid under pressure to pressure isolation valve 136, which transmits the mixed fluid to output conduit 138 and the patient catheter C for a balloon inflation procedure via a balloon inflation lumen. It will be understood, peristaltic pump 126 may be replaced by a syringe pump 40d(2) (not shown) or like pressurizing device, such as a pump disclosed in U.S. patent application Ser. No. 11/403,119, filed Apr. 12, 2006 and entitled "Fluid Delivery System with Pump Cassette", the disclosure of which was previously incorporated herein in its entirety by reference. The addition of a second pump device will result in a two fluid pump configuration much like that discussed previously in connection with FIG. 13. In such a substitution, second syringe pump 40d(2) or like device as described will typically be used as the balloon inflator. Additionally, in such a substitution, pressure isolation valve 136 may be replaced by a suitable fluid control valve to selective allow output from respective syringe pumps 40d(1), 40d(2) to pass to the catheter C as desired by the operator. As an alternative, syringe pump 40d may be connected to saline source 128 via an upstream connection from fluid control valve 124 which allows syringe pump 40d to draw from saline source 128 and operate as a balloon inflator in its own right if desired. It will be further noted that the pump disclosed in application Ser. No. 11/403,119 may be provided in place of pump 284 (or second syringe pump 240(2)) in system 200.

In the fluid injection mode, first automated fluid control valve 120 is initially operated to allow syringe pump 40d to be in fluid communication with first contrast source 122. Syringe pump 40d may be filled with a dose of contrast and aspirated as described previously in this disclosure. Once syringe pump 40d is prepared for an injection procedure, first automated fluid control valve 120 is operated to permit fluid communication between syringe pump 40d and pressure isolation valve 136. Syringe pump 40d may then be actuated by a system control associated with fluid control module 110 or syringe pump 40d itself deliver contrast under pressure to pressure isolation valve 136, which transmits the mixed fluid to output conduit 138 and a fluid injection lumen in patient catheter C. Primary or first contrast source 122 may be a more expensive non-ionic contrast while secondary contrast source 130 is a less expensive ionic contrast. System 10d may also comprise a check valve 142 in the low pressure side of reusable portion 114 of fluid path 70d to prevent fluid backup into first contrast source 122 and saline source 128. Further, system 10d may comprise a downstream fluid control valve 144 that is operable to isolate the patient catheter from system 10d or as a connection point to multiple lumen catheter C. It will be appreciated that fluid control valve 144 may be configured and operated such that it delivers "high" pressure contrast to one input lumen of catheter C (e.g., the fluid injection lumen) in one setting and low pressure mixed contrast and saline to the lower pressure lumen (e.g., balloon inflation lumen) of catheter C in another setting. Such settings may be coordinated with the operation of the pressure isolation valve 136 which transmits either high pressure fluid from syringe pump 40d or low pressure fluid from peristaltic pump 126 and fluid control valve 144 itself may be operated by fluid control module 110.

Figure 17:
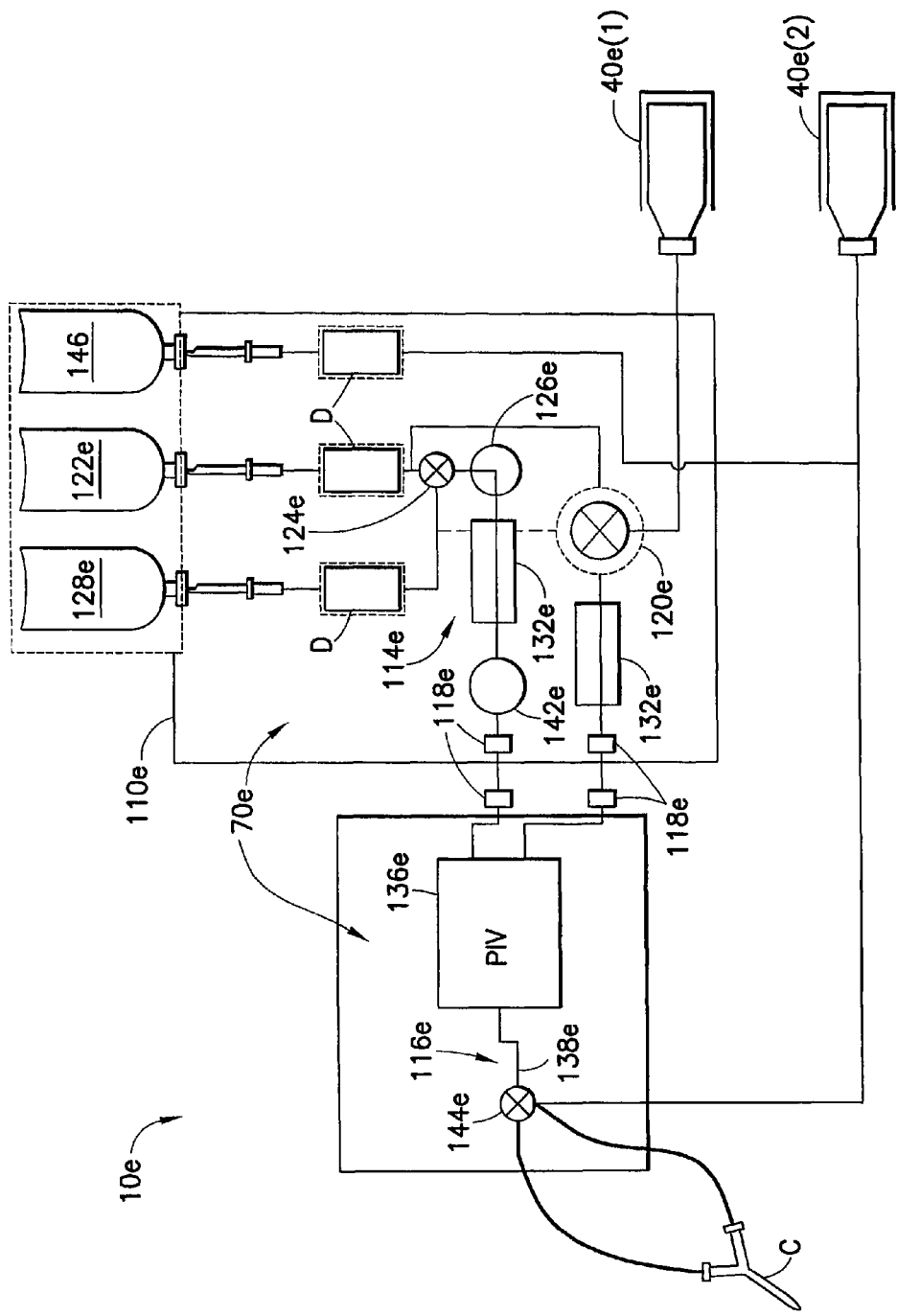
FIG. 17 is a schematic diagram of a variation of the fluid injection and inflation system of FIG. 16.

FIG. 17 illustrates a modification to system 10d described immediately above. System 10e is generally similar to system 10d with the addition of a second syringe pump 40e(2). Additionally, first syringe pump 40e(1) is connected directly to first contrast source 122e to draw contrast from this source. Second syringe pump 40e(2) is used as a vehicle to deliver a third fluid to the patient via the patient catheter. Second syringe pump 40e(2) is connected to a third fluid media source 146 which is typically a drug-containing fluid source or possibly even a premixed contrast-saline source enabling second syringe pump 40e(2) to operate as a balloon inflator via appropriate actuation of fluid control valve 144e. The output of second syringe pump 40e(2) is connected to downstream fluid control valve 144e and, therefore, bypasses pressure isolation valve 136e and may deliver the third fluid media directly to the patient catheter (e.g., fluid injection lumen) when valve 144e is open. It will be understood that first syringe pump 40e(1) is intended to remain as the primary injector for injecting contrast into the patient. As with system 10d shown in FIG. 16, peristaltic pump 126e may also be adapted for use as a balloon inflator due to the presence of second automated fluid control valve 124e, and peristaltic pump 126e may be replaced by a third syringe pump 40e(3) or other pump device as discussed previously in connection with FIG. 16. The addition of second syringe pump 40e(2) allows the operator to draw on a third fluid media as desired during either a balloon inflation or a high pressure fluid injection procedure involving contrast. While FIGS. 16 and 17 were discussed with reference to contrast, saline, and a drug containing fluid media as the three sources of fluid for use in systems 10d, 10e, these should be considered only as examples and systems 10d, 10e should not be read as being limited to these three specific fluids. Furthermore, it desired, a pressure relief valve or device may be provided in output line 138, 138e to regulate pressure within the catheter balloon and could, for example, be associated with downstream fluid control valve 144, 144e. Control valve 144, 144e may also include a dump port for emptying the contents of the inflated balloon (e.g., deflation) once it is desired to deflate the balloon. Alternatively, if a syringe or other disclosed pump is provided in place of peristaltic pump 126, 126e and forms the balloon inflator as in the foregoing examples, this pump may simply be operated in reverse to operate as the balloon "deflator". In conclusion, system 10 may also be interfaced with external devices for control and synchronization, such as automated valving, X-ray generators, computed tomography scanners, or film changers, such as is currently the practice with available vascular injection systems. It is also possible to connect system 10 to a printer or other devices that provide a hard copy output, or to hospital computer systems for additional information display and record keeping.

While several embodiments of a fluid injection and balloon inflation system and methods associated therewith were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

The invention claimed is:

1. A fluid injection and inflation system, comprising:
   a catheter comprising a fluid injection lumen and a balloon inflation lumen connected to a balloon;
   a first fluid source;
   a second fluid source;
   a fluid path to connect the first fluid source and the second fluid source to the catheter, the fluid injection lumen in fluid connection with the first fluid source and the balloon inflation lumen in fluid connection with the first fluid source and the second fluid source, the balloon inflation lumen operable to inflate the balloon;
   a fluid delivery system comprising a first pressurizing device and a second pressurizing device operably associated with the fluid path; and
   a control unit operable to control the fluid delivery system;
   wherein the control unit selectively actuates the fluid delivery system to operate in a fluid injection mode wherein the first pressurizing device delivers fluid from the first fluid source to the fluid injection lumen for a fluid injection procedure, and in a balloon inflation mode wherein the second pressurizing device delivers a mixture of fluids from the first fluid source and the second fluid source to the balloon inflation lumen for a balloon inflation procedure wherein the balloon is inflated with the mixture of fluids.

2. A fluid injection and inflation system as claimed in claim 1, wherein the control unit comprises an operator interface to input fluid injection mode and balloon inflation mode control parameters.

3. A fluid injection and inflation system as claimed in claim 1, wherein the first pressurizing device and the second pressurizing device each comprise a syringe pump and the control unit controls operation of the syringe pumps via a pump controller.

4. A fluid injection and inflation system as claimed in claim 1, further comprising an operator control connected to the control unit.

5. A fluid injection and inflation system as claimed in claim 4, wherein the operator control comprises a handheld control device.

6. A fluid injection and inflation system as claimed in claim 1, wherein the first pressurizing device comprises a syringe pump.

7. A fluid injection and inflation system as claimed in claim 1, wherein the first fluid source comprises contrast and the second fluid source comprises a diluent.

8. A fluid injection and inflation system as claimed in claim 1, wherein the first pressurizing device is selectively connectable to at least two different fluid sources and the second pressurizing device is selectively connectable to a third fluid source.

9. A fluid injection and inflation system as claimed in claim 8, wherein the first pressurizing device delivers fluid from the first fluid source to the fluid injection lumen in the fluid injection mode and delivers a mixture of fluids from the first fluid source and the second fluid source to the balloon inflation lumen in the balloon inflation mode.

10. A fluid injection and inflation system as claimed in claim 8, wherein the second pressurizing device delivers fluid from the third fluid source to the fluid injection lumen in the fluid injection mode.

11. A fluid injection and inflation system as claimed in claim 10, wherein the third fluid source comprises a drug-containing fluid.

12. A fluid injection and inflation system as claimed in claim 1, wherein the fluid injection lumen is coaxial around the balloon inflation lumen.

13. A fluid injection and inflation system as claimed in claim 1, wherein the second pressurizing device comprises a syringe pump.

14. A method of delivering fluid to a catheter, comprising:
   providing a fluid delivery system comprising:
      a catheter comprising a fluid injection lumen and a balloon inflation lumen connected to a balloon;
      a first fluid source;
      a second fluid source;
      a fluid path to connect the first fluid source and the second fluid source to the catheter, the fluid injection lumen in fluid connection with the first fluid source and the balloon inflation lumen in fluid connection with the first fluid source and the second fluid source, the balloon inflation lumen operable to inflate the balloon;
      a fluid delivery system comprising a first pressurizing device and a second pressurizing device operably associated with the fluid path; and
      a control unit operable to control the fluid delivery system;
   inputting fluid injection and/or balloon inflation parameters into the control unit for performing a fluid injection procedure and/or a balloon inflation procedure; and
   selectively actuating the operator control to perform either the fluid injection procedure wherein the first pressurizing device delivers fluid from the first fluid source to the fluid injection lumen, or the balloon inflation procedure wherein the second pressurizing device delivers a mixture of fluids from the first fluid source and the second fluid source to the balloon inflation lumen to inflate the balloon in accordance with the fluid injection or balloon inflation parameters inputted into the control unit.

* * * * *

UNITED STATES PATENT AND TRADEMARK OFFICE
CERTIFICATE OF CORRECTION

| | |
|---|---|
| PATENT NO. | : 8,192,397 B2 |
| APPLICATION NO. | : 11/425497 |
| DATED | : June 5, 2012 |
| INVENTOR(S) | : Griffiths et al. |

It is certified that error appears in the above-identified patent and that said Letters Patent is hereby corrected as shown below:

IN THE SPECIFICATION

In Column 8, Line 16, delete "pre-identified indentified" and insert -- pre-identified --, therefor.

In Column 12, Line 32, delete "biocompatable" and insert -- biocompatible --, therefor.

IN THE CLAIMS

In Claim 2, Column 25, Line 40, delete "injection mode and balloon" and insert -- injection mode control parameters and balloon --, therefor.

Signed and Sealed this
Twenty-fifth Day of June, 2013

Teresa Stanek Rea
*Acting Director of the United States Patent and Trademark Office*